US010780234B2

(12) United States Patent
Lee

(10) Patent No.: US 10,780,234 B2
(45) Date of Patent: Sep. 22, 2020

(54) DENTAL SYRINGE WITH STABILIZER FOR REMOVABLE NEEDLE

(71) Applicant: Alexander E Lee, Closter, NJ (US)

(72) Inventor: Alexander E Lee, Closter, NJ (US)

( * ) Notice: Subject to any disclaimer, the term of this patent is extended or adjusted under 35 U.S.C. 154(b) by 380 days.

(21) Appl. No.: 15/552,493

(22) Filed: Aug. 21, 2017

(65) Prior Publication Data
US 2018/0104420 A1    Apr. 19, 2018

Related U.S. Application Data

(63) Continuation-in-part of application No. PCT/US2016/018587, filed on Feb. 19, 2016.
(Continued)

(51) Int. Cl.
*A61M 5/32* (2006.01)
*A61M 5/24* (2006.01)
(Continued)

(52) U.S. Cl.
CPC .......... *A61M 5/3269* (2013.01); *A61M 5/002* (2013.01); *A61M 5/24* (2013.01); *A61M 5/31515* (2013.01); *A61M 5/346* (2013.01); *A61M 2005/2414* (2013.01); *A61M 2005/2488* (2013.01); *A61M 2210/0625* (2013.01)

(58) Field of Classification Search
CPC ...... A61M 5/3269; A61M 5/002; A61M 5/24; A61M 5/31515; A61M 5/346; A61M 2005/2414; A61M 2005/2488; A61M 2210/0625
See application file for complete search history.

(56) References Cited

U.S. PATENT DOCUMENTS 1,012,700 A   12/1910 Payne
1,532,744 A   4/1924 Hein
(Continued)

OTHER PUBLICATIONS

By Wilburta Q. Lindh, Marilyn Pooler, Carol D. Tamparo, Barbara M. Dahl; Combination Disposable/Nondisposable Cartridge Injection Systems; 5th ed., 2014, p. 792, Fig. 24-10, "The Carpuject is a type of cartridge-injection system with a click-lock mechanism for safety." book: Delmar's Clinical Medical Assisting, isbn= 1133603408, Publisher: Delmar, Steven Helba, Clifton Park, NY, US, 2013.
(Continued)

*Primary Examiner* — Lauren P Farrar
(74) *Attorney, Agent, or Firm* — Collard & Roe, P.C.

(57) ABSTRACT

A cartridge syringe system includes a syringe (5). The syringe has a tip-ward direction and a ring-ward direction. The syringe (5) has a syringe body (9) and an actuator ring (7). A shaft (10) slidably mounts the actuator ring (7) to the syringe body (9), with a harpoon (11) at a tip-ward end of the shaft (10). The syringe body (9) has a spiral mount external to the syringe body (9) for removably mounting a sheath (20) to the syringe body (9), on a cooperating internal spiral sheath mount. The syringe body (9) and the sheath have similar openings. The sheath opening can be rotated to coincide with the syringe body opening, for inserting a needle assembly into the syringe body, or for removing the needle assembly. The sheath opening can be rotated to obstruct the syringe body opening, for retaining the needle assembly in the syringe body.

12 Claims, 19 Drawing Sheets

Related U.S. Application Data

(60) Provisional application No. 62/118,310, filed on Feb. 19, 2015.

(51) Int. Cl.
    *A61M 5/315*     (2006.01)
    *A61M 5/34*     (2006.01)
    *A61M 5/00*     (2006.01)

(56) References Cited

U.S. PATENT DOCUMENTS

| | | | |
|---|---|---|---|
| 2,147,616 A | | 2/1939 | Chaput |
| 2,169,371 A | * | 8/1939 | Payne .................. A61M 5/344 604/242 |
| 2,956,563 A | | 10/1960 | Sarnoff |
| 3,848,593 A | | 11/1974 | Baldwin |
| 4,892,525 A | | 1/1990 | Hermann, Jr. et al. |
| 4,931,040 A | | 6/1990 | Haber |
| 5,069,225 A | * | 12/1991 | Okamura .............. A61M 5/348 600/578 |
| 5,205,827 A | | 4/1993 | Novacek et al. |
| 5,501,670 A | * | 3/1996 | Sak .................... A61M 5/31511 604/110 |
| 6,764,471 B2 | | 7/2004 | Lee |
| 8,128,605 B2 | | 3/2012 | Masi et al. |
| 2002/0004647 A1 | | 1/2002 | Leong |
| 2011/0068034 A1 | * | 3/2011 | Hwang ................ A61M 5/002 206/515 |

OTHER PUBLICATIONS

Yagme12, Carpuject, https://www.youtube.com/watch?v=ICJYr-0VIrA YouTube video, & Screen-grabs from said video, publisher: yagme12, Published on Apr 1, 2014, city and/or country where published: unknown.

Photo of three Carpuject metal syringes, assembled to screw-on needles. Standardized medicine vials are to be inserted into the syringe bodies. The syringes or similar designs may date to the 1950s.

Carpuject, From Wikipedia, https://en.wikipedia.org/wiki/Carpuject, The Carpuject is a syringe for the administration of injectable fluid. It was patented by the Sterling Drug Company, which became the Sterling Winthrop, after World War II. The Carpuject competed with the Tubex injection system developed by Wyeth. Redesigned several times. In 1988 Kodak purchased Winthrop Labs. 1994 sold to Sanofi, a French pharmaceutical company, now Sanofi Aventis. In 1997 Sanofi sold to Abbott Laboratories. 2004 Abbott separated its hospital supply line: Hospira, May 30, 2017.

Tubex, The Tubex Syringe cartridge developed c. 1943 during World War II by the Wyeth company. It is a drug pre-filled glass cartridge syringe with attached sterile needle, which is inserted in a reusable stainless steel holder (now plastic). https://en.wikipedia.org/wiki/Tubex_(syringe_cartridge).

International Search Report in PCT/US16/18587, dated Apr. 29, 2016.

* cited by examiner

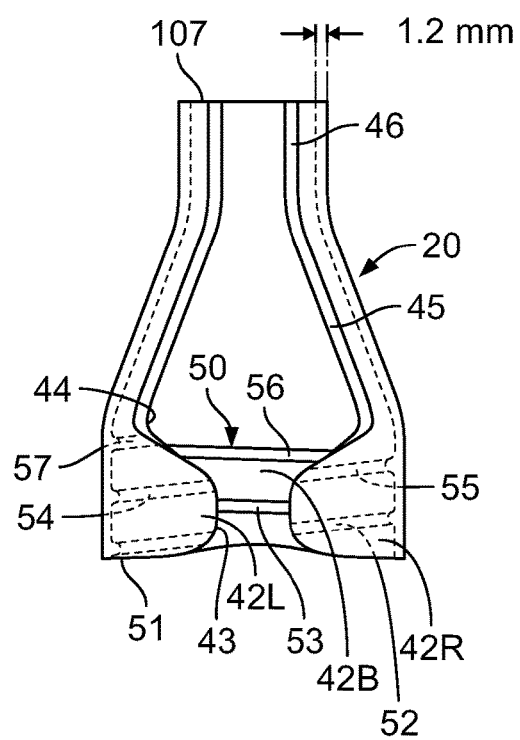
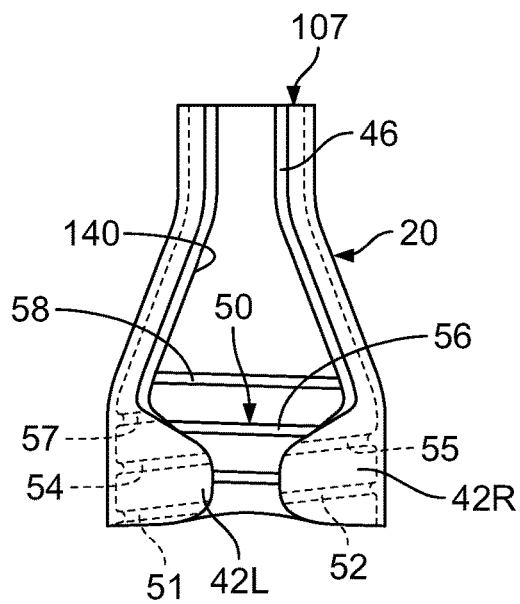
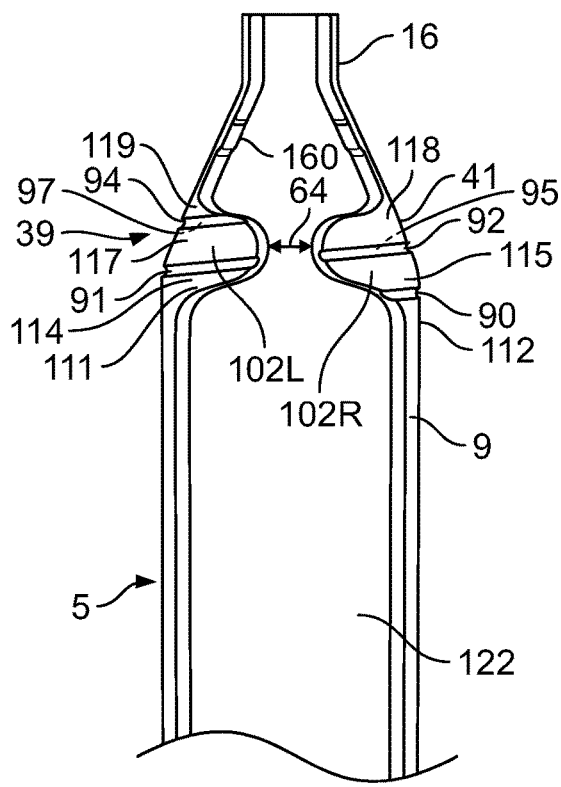
FIG. 4
FIG. 5

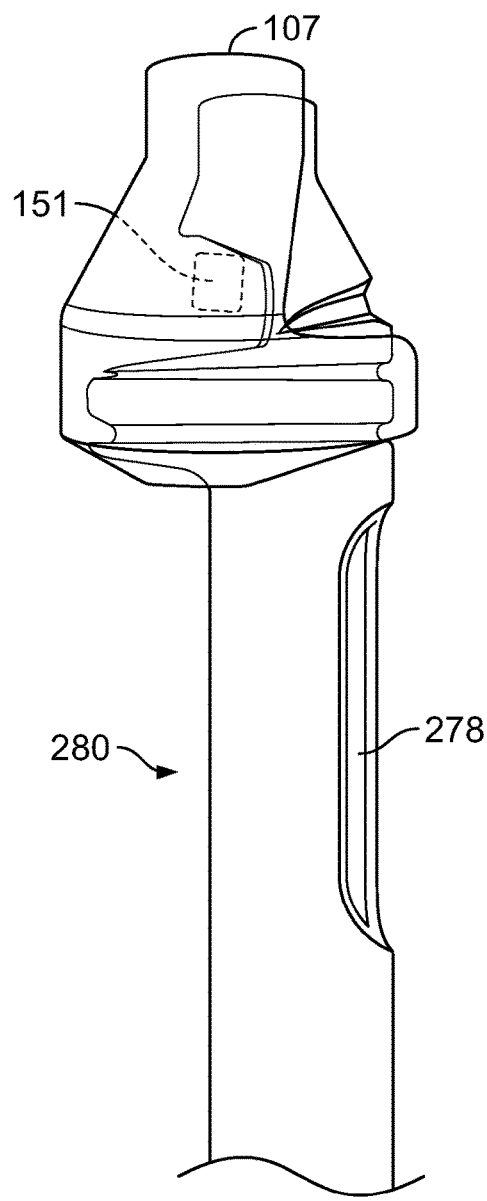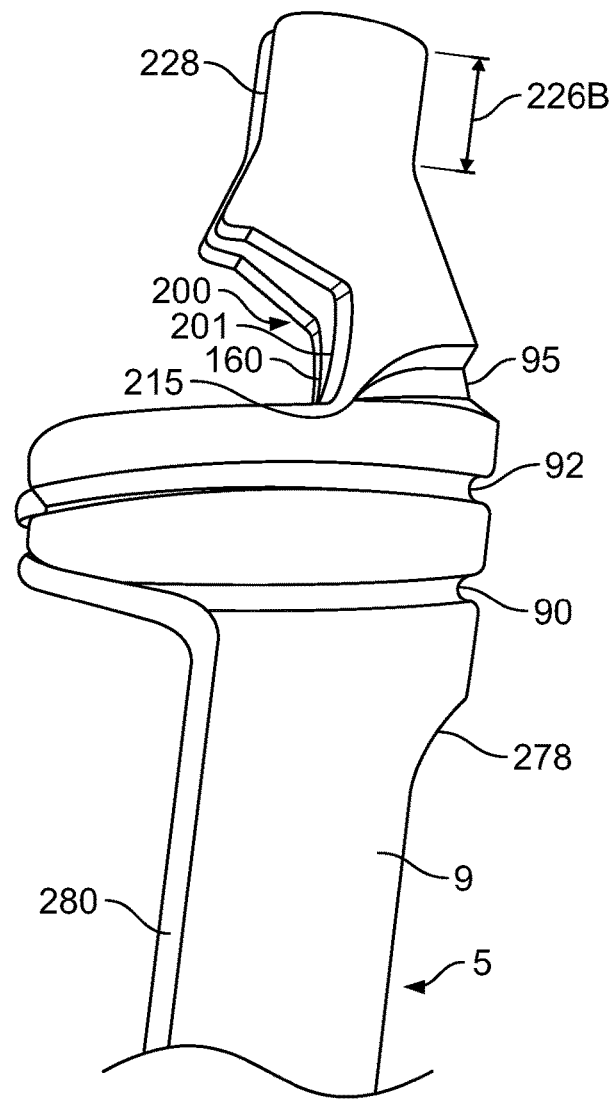
FIG. 11
FIG. 12

DENTAL SYRINGE WITH STABILIZER FOR REMOVABLE NEEDLE

This application is a PCT Bypass Continuation in Part Application taking priority and benefit of all common subject matter of:

U.S. Provisional Patent Application 62/118,310 filed 19 Feb. 2015; and PCT/US16/18587 filed 19 Feb. 2016.

FIELD OF THE INVENTION

The present invention relates to a new type of dental syringe system.

DESCRIPTION OF THE RELATED ART

In the dental syringe art, the conventional syringe is adapted to allow the dentist to retract the syringe plunger after the initial stick, in order to ascertain that he has not hit a blood vessel, by using his thumb in the thumb ring of the syringe, pulling back on the plunger and observing the anesthetic vial to determine if blood has been pulled into the syringe. If it has, this indicates that he must find a new spot for the injection point in order to avoid injecting anesthetic into the bloodstream via a blood vessel. There are two reasons for this:

1. The anesthetic usually contains epinephrine, which can affect heart rate adversely.

2. If the anesthetic is taken away from the site by the blood vessel, it will fail to anaesthetize the site.

Thus, in contrast to the usual medical syringe used by doctors, in which the entire syringe is generally disposable, the dental syringe has a reusable metal framework. Medication is usually in a disposable cartridge. So this type of syringe is also known as a cartridge syringe.

BACKGROUND OF THE INVENTION

The closest reference we are aware of in the art is the Present Inventor's earlier patent U.S. Pat. No. 6,764,471 B2, Granted: Jul. 20, 2004, on application number: U.S. Ser. No. 10/008,373 Filing date Nov. 13, 2001, Priority date Nov. 13, 2000

The present invention improves on the disclosure of said present inventor's prior patent. U.S. Pat. No. 6,764,471 B2 is hereby incorporated by reference.

Hospira™ (part of Abbott Labs™) has Carpuject™ syringes.

See: http://en.wikipedia.org/wiki/Carpuject
https://www.youtube.com/watch?v=r4a9E4oV6jY

BRIEF DESCRIPTION

The present invention provides a sheath, which snaps or screws on to threads on the needle-end, or tip, of the syringe to stabilize the needle during injection. This sheath will be made out of either plastic or metal and clipped onto the syringe.

This sheath will allow the insertion of a needle assembly, in the sheath's resting position.

We will define axial directions used in this application as:
Tip-ward=towards the needle tip; and
Ring-ward=toward the thumb ring or actuator ring=the opposite direction to tip-ward.

After insertion of the needle, this sheath will be rotated to push the needle assembly tip-ward, thereby seating a conical segment of the needle assembly, against a cooperatively shaped conical part of the interior of the syringe body's tip-ward end.

The sheath will thus stabilize the needle, and thereby facilitate changing anesthetic cartridges during multiple injections.

Further rotation of the sheath will cause the flexible sheath to jump the threads on the syringe and thereby relieve the seating pressure and allow the needle to fall from the syringe into a sharps container.

Alternatively, reversing rotation of the sheath will also relieve the seating pressure and allow the needle to fall from the syringe into a sharps container.

BRIEF DESCRIPTION OF THE DRAWINGS

FIG. 4 is a front elevation of the sheath.

FIG. 5 is a front elevation of the tip-ward end of the syringe, without the sheath.

FIG. 11 is a side elevation of the sheath on the syringe.

FIG. 12 is a side elevation of the syringe.

DETAILED DESCRIPTION OF THE DRAWINGS

Figure 1:
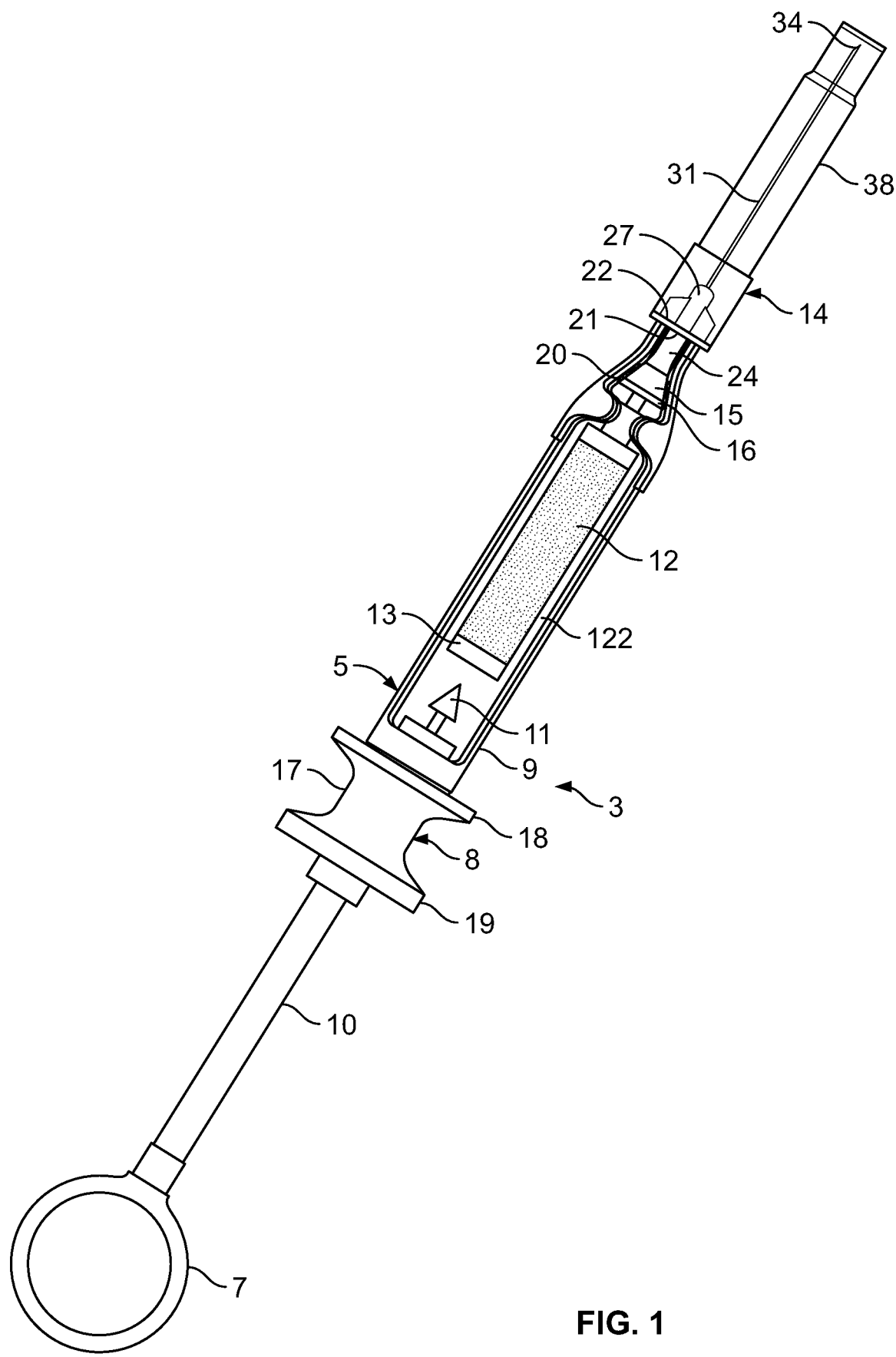
FIG. 1 is a front elevation, of a dental syringe system of the present invention.

FIG. 1 is a front elevation, of the present invention, which provides a dental syringe system. A dental syringe is also known as a cartridge syringe. There are some applications for this syringe and needle system, in the general medical field. If the medications are supplied in the cartridge form rather than a vial or ampule, then this cartridge syringe system can deliver the medications more: easily, simply, and safely.

The prior art requires a user to:

aspirate the medications from the vials and ampules into the medical grade disposable (plastic) syringes, which typically use a large bore needles (20 or 22 gauge); and then inject the medications into a person.

The present invention can deliver the medications using the smaller bore needles, if the medications are placed into the cartridge form.

The system, when assembled, forms an assembly which is generally designated 3.

A syringe 5 comprises a thumb ring 7, and a finger grip 8, on a syringe body 9.

I will hereinafter describe and clam the thumb ring 7 as an actuator ring 7, to avoid claiming a human body part, the thumb.

Shaft 10 slidably mounts actuator ring 7 to syringe body 9. At the tip-ward end of shaft 10 is a harpoon 11.

A medicine cartridge 12 is mountable in syringe body 9 of syringe 5. Medicine cartridge 12 has a slidable seal 13, into which harpoon 11 can be inserted and anchored to form a plunger (13, 11, 10, & 7) with shaft 10, which can then be slid: needle-ward; or ring-ward; by manipulating the actuator ring 7 in those directions. The ring-ward direction will be referred to in the claims as a ring-ward direction. The actuator ring 7 is configured to be controlled by a thumb, controlling the actuator ring 7 to expand or contract the volume of the cartridge.

Finger grip 8 comprises a recess 17, and a pair of flanges axial to the recess 17:

tip-ward finger flange 18, and ring-ward finger flange 19.

But before harpoon 11 is inserted into the cartridge, needle assembly 14 is placed with a conical portion 15 seated inside the matching conical end 16 of syringe body 9. A removable sheath 20 is configured to retain the needle assembly in the syringe body 9.

The syringe body 9 has an external spiral mount 40 on the cylindrical portion of syringe body 9. The external spiral mount 40 includes a threaded matching groove or thread on the outside of the cylindrical portion of syringe body 9.

The sheath 20 has an internal spiral mount 50, which comprises an internal thread 50, having thread segments: 51, 52, 53, 54, 55, 56, & 57.

The sheath 20 and its internal thread 50 may be rotated in a loosening direction, which would be counter-clockwise when viewed from the tip-ward end. This clockwise rotation causes the tip-ward end 21 of sheath 20 to push against flange 22 on a cylindrical portion 27 of needle assembly 14, and thereby seat conical portion 15 of needle assembly 14 firmly against matching internal, conical end 16 of syringe body 9.

Sheath 20 will be made out of a plastic which has a melting temperature above 137 degrees Celsius so that the sheath 20 may be for autoclaved. The sheath plastic should also be somewhat elastic (to allow insertion and removal from the syringe), and relatively cheap and easy to manufacture. The presently preferred plastic is nylon. The sheaths 20 are disposable (after multiple uses). New sheaths can be bought separately.

Needle 31 has a point 34.

Needle 31 and point 34 are supplied covered by a safety cap 38, protecting a user from the point 34 of needle 31.

Syringe body 9 comprises a spiral groove or grooves 39, in a grooved part 40 of syringe body 9. The groove is preferably on a cylindrical part of an outside surface of the syringe body 9. The groove is spiral.

Figure 9:
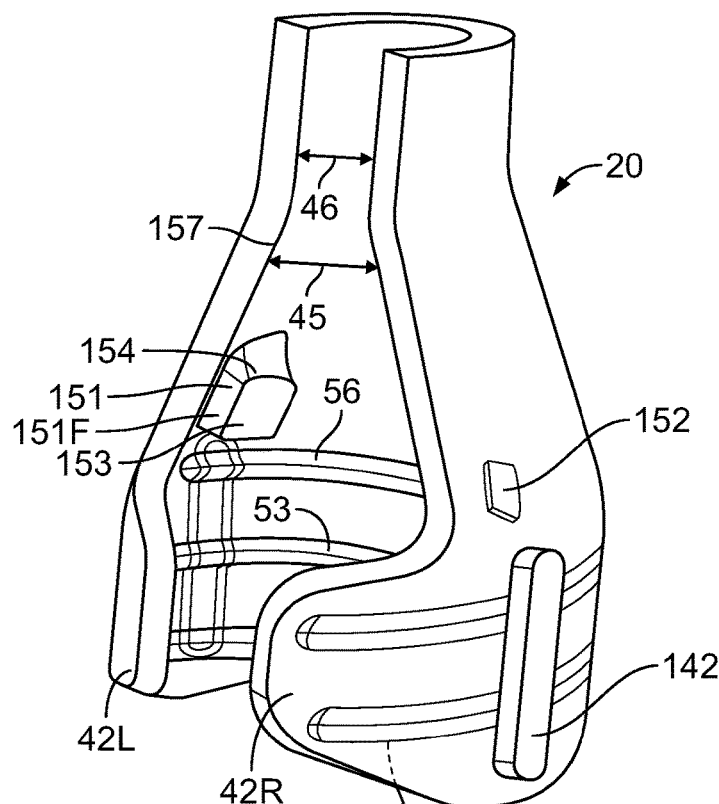
FIG. 9 is a front oblique view of the sheath.

FIGS. 1, 4, 5 & 6, & 10 show front views of sheath 20. Sheath front 42 (FIG. 10) has a left side 42L and right side 42R. Front 42 is open at varying widths at 43-44 (FIG. 10); 45 & 46 (FIG. 9).

Figure 2:
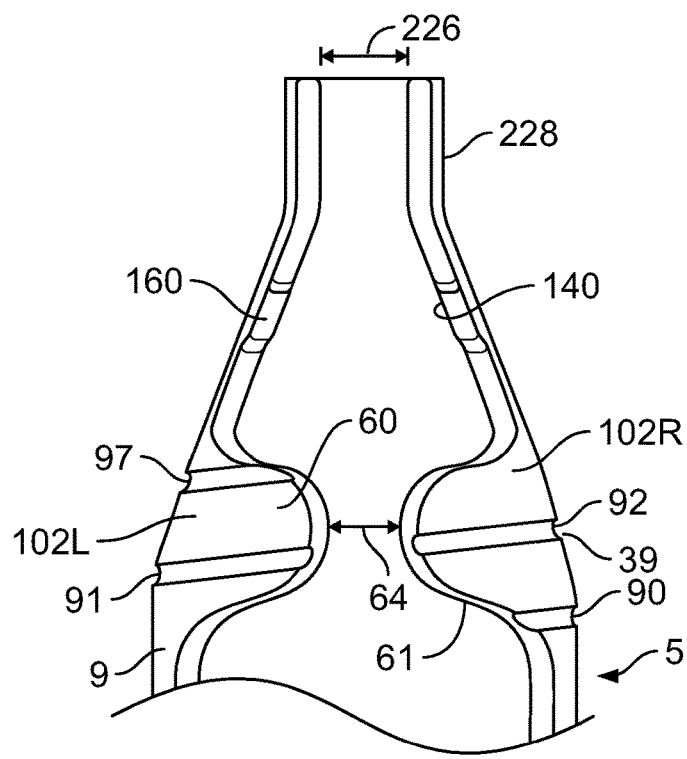
FIG. 2 is a front elevation of part of a syringe of the present invention.
Figure 3:
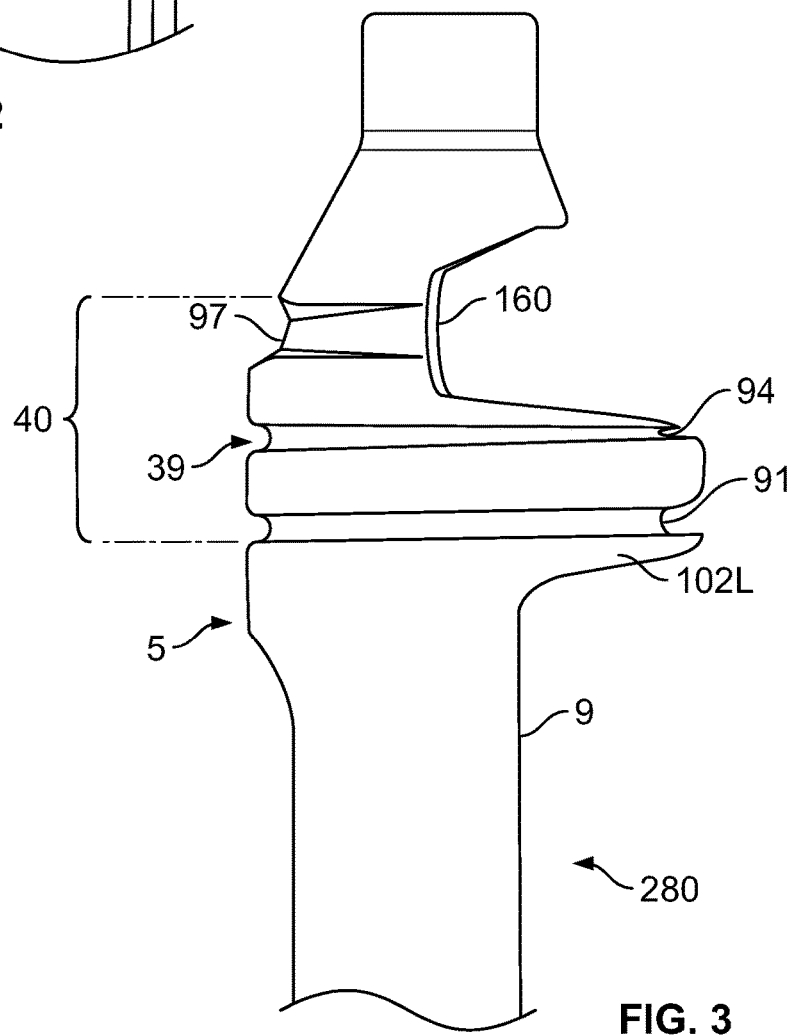
FIG. 3 is a side elevation thereof.

In FIG. 4, internally threaded sheath 20, snaps and/or screws by threads 50, in segments 51-57; on to grooves 39, shown in FIG. 2 front elevation; in FIG. 3 side elevation; and FIG. 5 exploded view.

FIG. 2 is a front elevation of the tip-ward end of the syringe 5 syringe body 9, without the sheath. Syringe front walls 102L & 102R are separated by a front gap 64 to allow the needle assembly 14 to be inserted.

Figure 19:
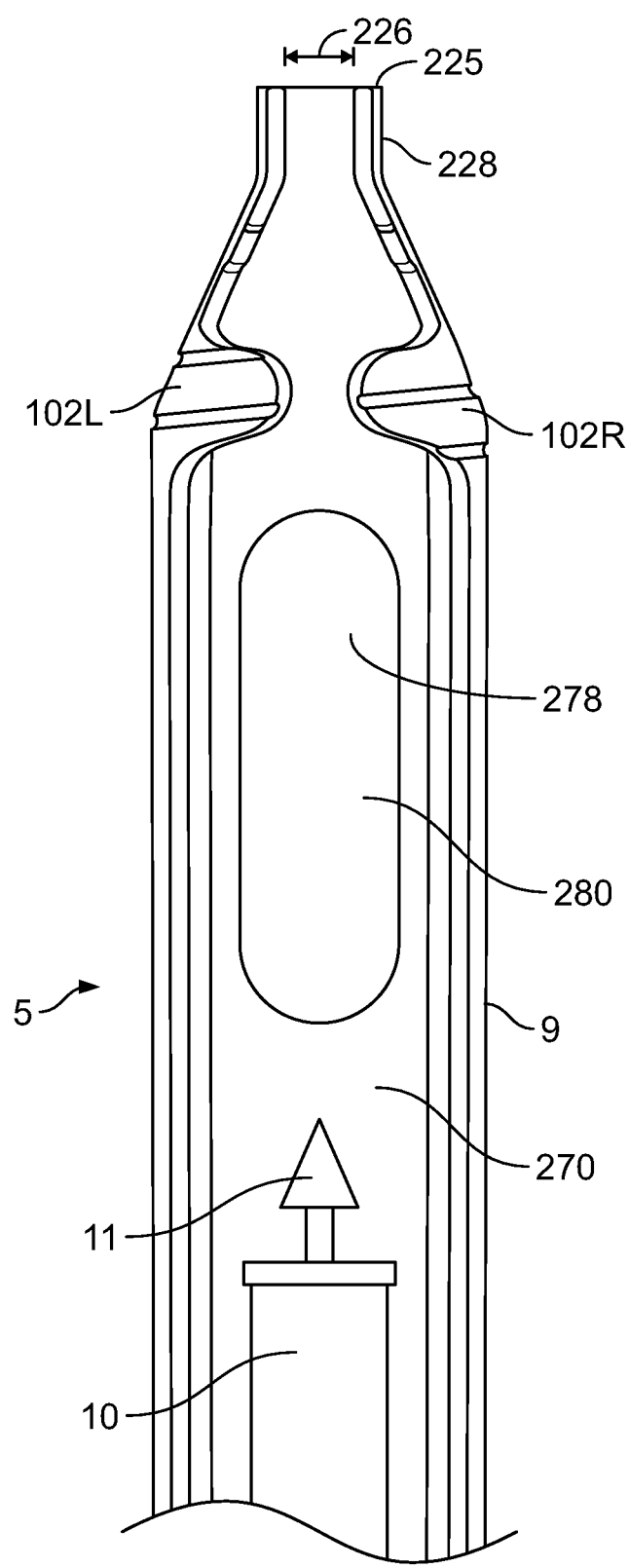
FIG. 19 is a front elevation of said syringe body with the shaft mounted on the body.

In the photos that were FIGS. 2 & 19 of the Provisional Application 62/118,310, a non-functional piece of paper was placed against the back-wall so the front walls 102L & 102R and gap 64 could be seen in FIG. 19 without being confused by back wall reflections of the stainless steel syringe body 9.

FIG. 3 is a side elevation of the tip-ward end of the syringe 5 including syringe body 9, without the sheath. Grooved part 40 comprises groove 39. Groove segments 91-97 are separated by lands 111-119.

FIG. 4 is a front elevation of sheath 20, which sheath 20 will be made out of either plastic or metal and clipped onto the syringe. The presently preferred embodiment is clear nylon with a wall thickness of 1.2 mm. It is softer than the metal syringe, and elastically flexible, so that it springs open and closed a little. The sheath must be autoclavable. The front 42 of sheath 20 is open at gaps of varying widths at 43, 44 (FIG. 10), 45 to 46 (FIG. 9), to allow needle assembly 14 to be inserted into the syringe body 9 from the front.

A protruding thread 50, matches the groove 39 (FIG. 5) on the grooved part 40 of syringe body 9.

As on FIG. 4, thread 50 begins ring-ward at segment 51 on front-wall 42L, is interrupted at gap 43, continues at segment 52 continuously around the back-wall 42B as segment 53, continues continuously as segment 54 around inside the front-wall 42L, is interrupted at gap 43, continues at segment 55 continuously inside the front-wall 42R, continuously around the back-wall 42B as segment 56, continues continuously as segment 57 around inside the front-wall 42L, and segment 57 ends at the gap at 44, the tip-ward end of thread 50.

FIG. 5 shows corresponding groove segments 91, 92, 94, 95, 97 on syringe body 9.

Grooves 91-97 divide lands 111, 112, 114, 115, 117, 118, 119, the raised parts between the depressed groove segments 91-97.

Figure 6:
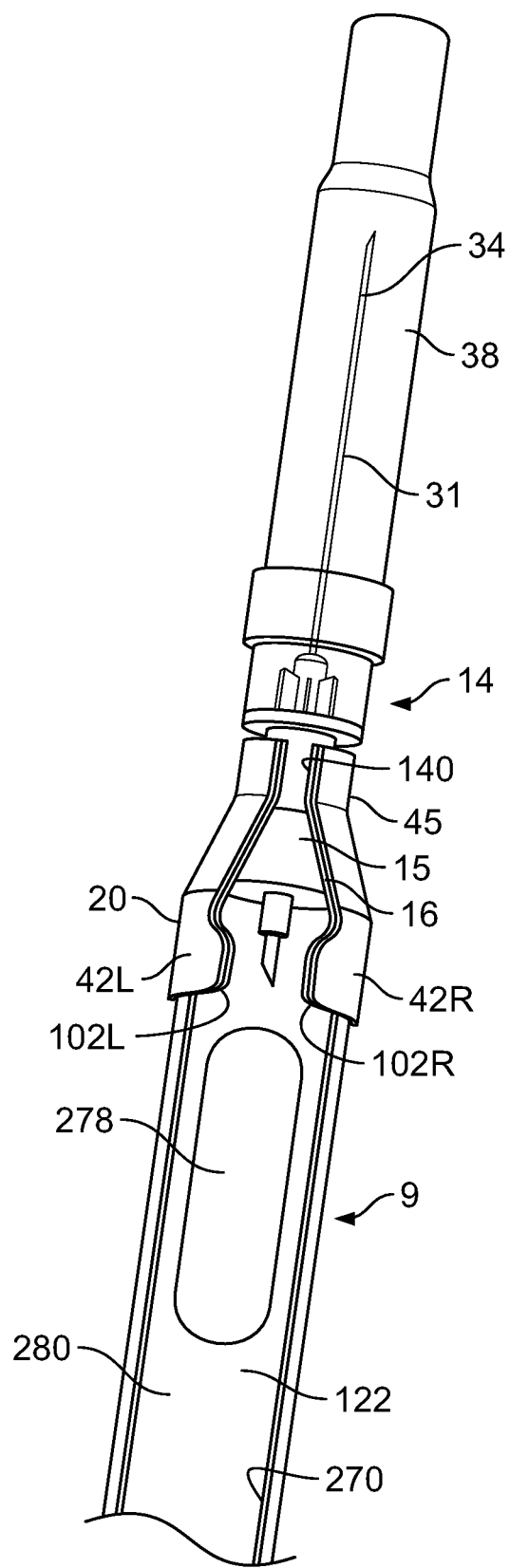
FIG. 6 is a front lower perspective view of the syringe, sheath in position to receive a needle assembly, and a needle assembly.

Sheath 20 should be installed on syringe 5 syringe body 9, first. This can be done by:

Placing sheath 20 needle ward of conical part 16, and spinning sheath 20 in a tightening direction until thread 50 grabs groove 39 and continuing to tighten, past some stops, until a stop at the position shown in FIGS. 1 & 6.

Or:

Placing sheath 20 tip-ward of conical part 16; and pushing down on tip 107 of sheath 20.

Thread segment 51 rides over land 117, to snap into groove 94 while thread segment 52 rides over land 115, to snap into groove 92.

A further push on tip 107 causes:

thread segment 51 to ride over land 114, to snap into groove 91, while thread segment 52 rides over land 115, to snap into groove 92; while thread segment 54 rides over land 117, to snap into groove 94, while thread segment 55 rides over land 115, to snap into groove 92.

Sheath 20 is now positioned as shown in FIGS. 1 & 6, ready to receive the needle assembly 14.

This sheath 20 will allow the insertion of a needle assembly 14, in the sheath 20's resting position, shown in FIGS. 1 & 6. Needle cone 15 is inserted through gap 45 of sheath 20, to seat against the inside 140 of syringe cone 16.

FIG. 6 is a front elevation of the syringe, sheath in position to receive a needle assembly, and a needle assembly. placed in the syringe, but not yet secured. A cartridge ejection slot 278 is provided.

In FIG. 1, to eject a medicine cartridge 12:
 withdraw actuator-ring 7, and harpoon 11 ring-ward;
 turn the syringe front-down over a waste container; and
 push a finger through cartridge ejection slot 278 against the medicine cartridge 12, until it falls out the long body front opening 122 on the front of syringe body 9 (FIG. 1).

To remove a needle assembly 14, reversing rotation of the sheath 20 will relieve the seating pressure and allow the needle assembly 14 to fall directly from the syringe into a sharps container by inverting the syringe (over the sharps container).

At this point it's useful to fully describe and show the details of the presently preferred sheath 20.

Figure 7:
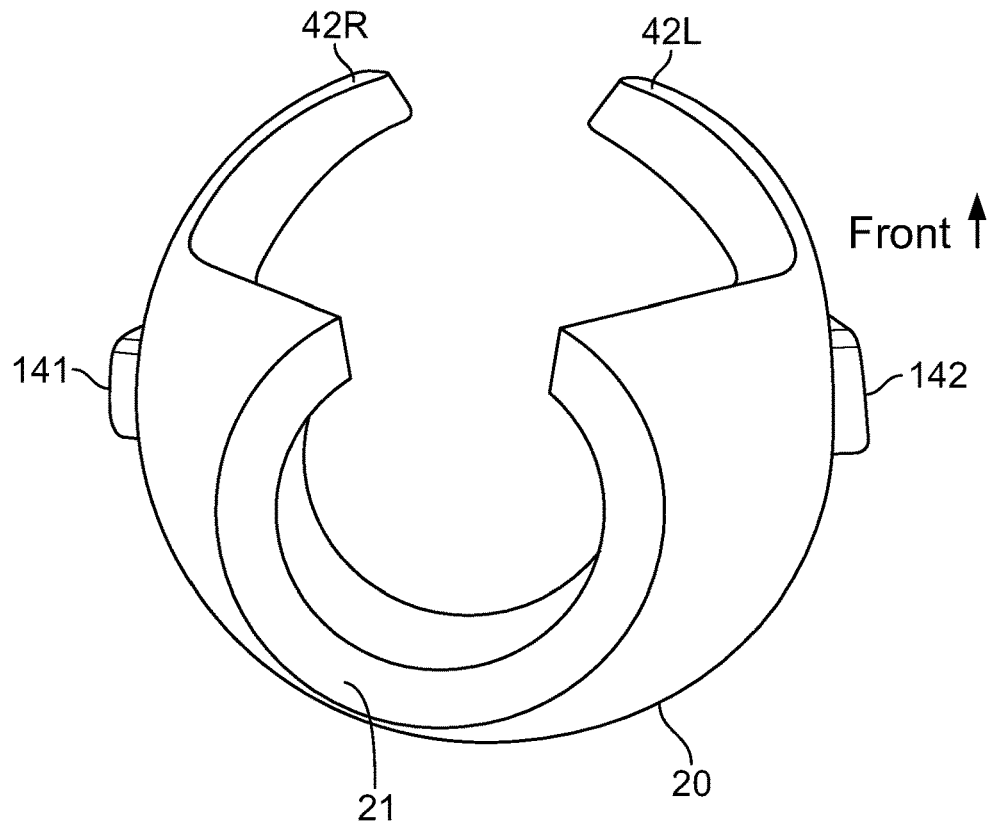
FIG. 7 is a slightly oblique top perspective view of the sheath 20, looking in a thumb-ward direction.

FIG. 7 is a slightly oblique top perspective view of sheath 20, looking in a ring-ward direction. Finger ribs 141 & 142, on the outside of sheath 20, assist the dentist in rotating the sheath by providing grip. Tip-ward end 21 is the surface which pushes against (FIG. 1) flange 22 on a cylindrical portion 27 of needle assembly 14.

Figure 8:
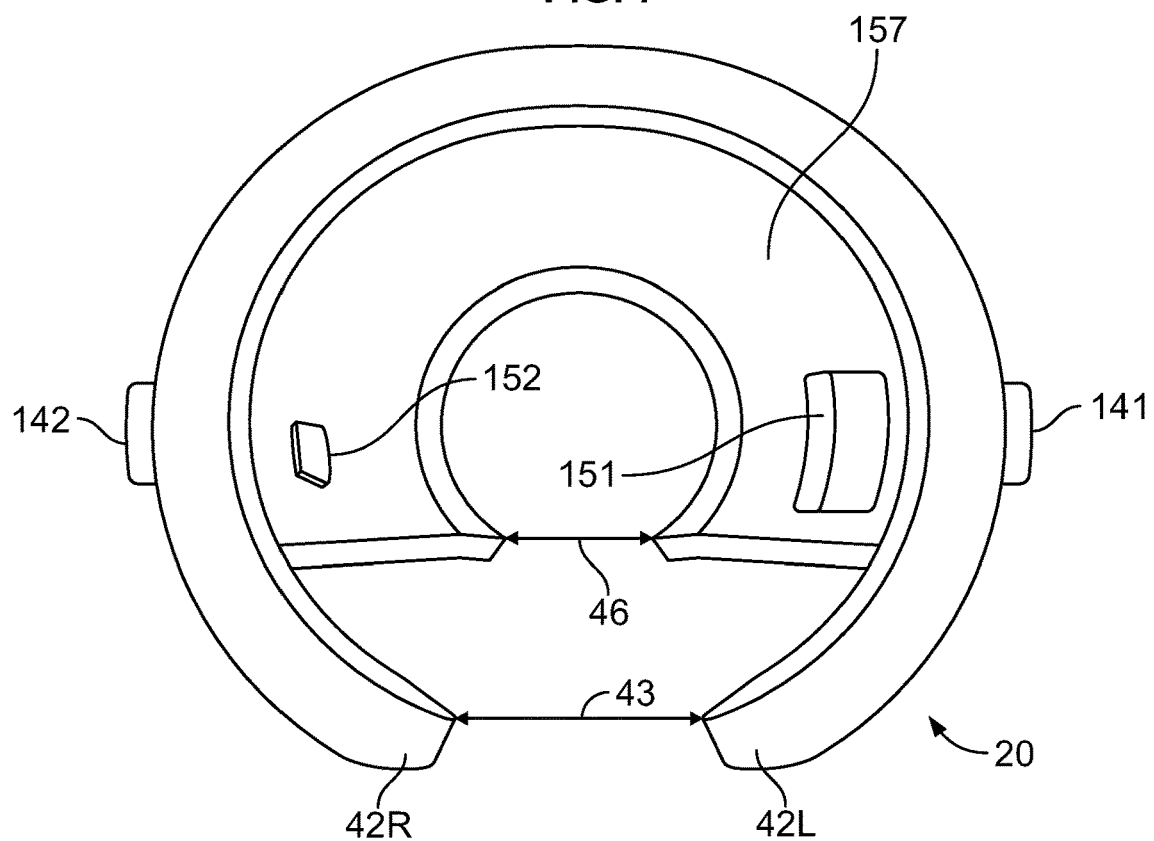
FIG. 8 is a bottom plan view of the sheath, looking in a tip-ward direction.

FIG. 8 is a bottom plan view of sheath 20, looking in a tip-ward direction. Internal stops 151 & 152 cooperate with surfaces and grooves on the syringe 5 to stop rotation of sheath 20 at various angles to syringe 5.

FIG. 9 is a front oblique view of sheath 20. This conveys the ramped and angled shape of stop 151. The angled surfaces of stop 151, include stop 151's front surface 151F, inside 153, and top 154. Sheath 20 has an inside wall 157.

Smaller stop 152 is seen through the translucent wall of sheath 20, as are thread segments 52, 53, and 56.

Figure 10:
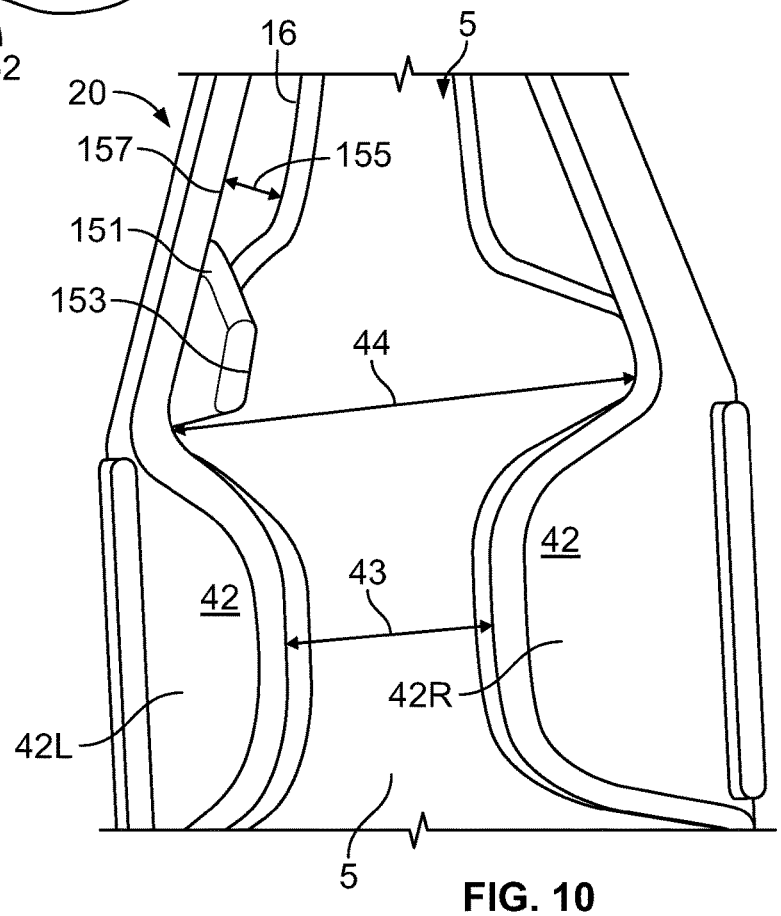
FIG. 10 shows clearance 155 between inside wall 157 of sheath 20, and outside of conical wall 16 of syringe 5.

FIG. 10 shows clearance 155 between inside wall 157 of sheath 20, and outside of conical wall 16 of syringe 5. In the position shown in FIG. 10, when the sheath 20 is being rotated onto syringe 5, and the lowest segment of the thread is engaged with the highest groove of the syringe 5, there is sufficient clearance 155 so that inside surface 153 of stop 151 almost clears the outside surface 16 of syringe 5, and provides only a gentle stop. Rotating sheath 20 tighter, expands flexible sheath 20, and allows sheath 20 to rotate another revolution, and ring-ward.

Because surface 157 approaches surface 16, the rotation becomes stiffer, until stop 151 (FIG. 11) drops into gap 200 (FIG. 12), at edge 201, at which point resistance drops.

Figure 13:
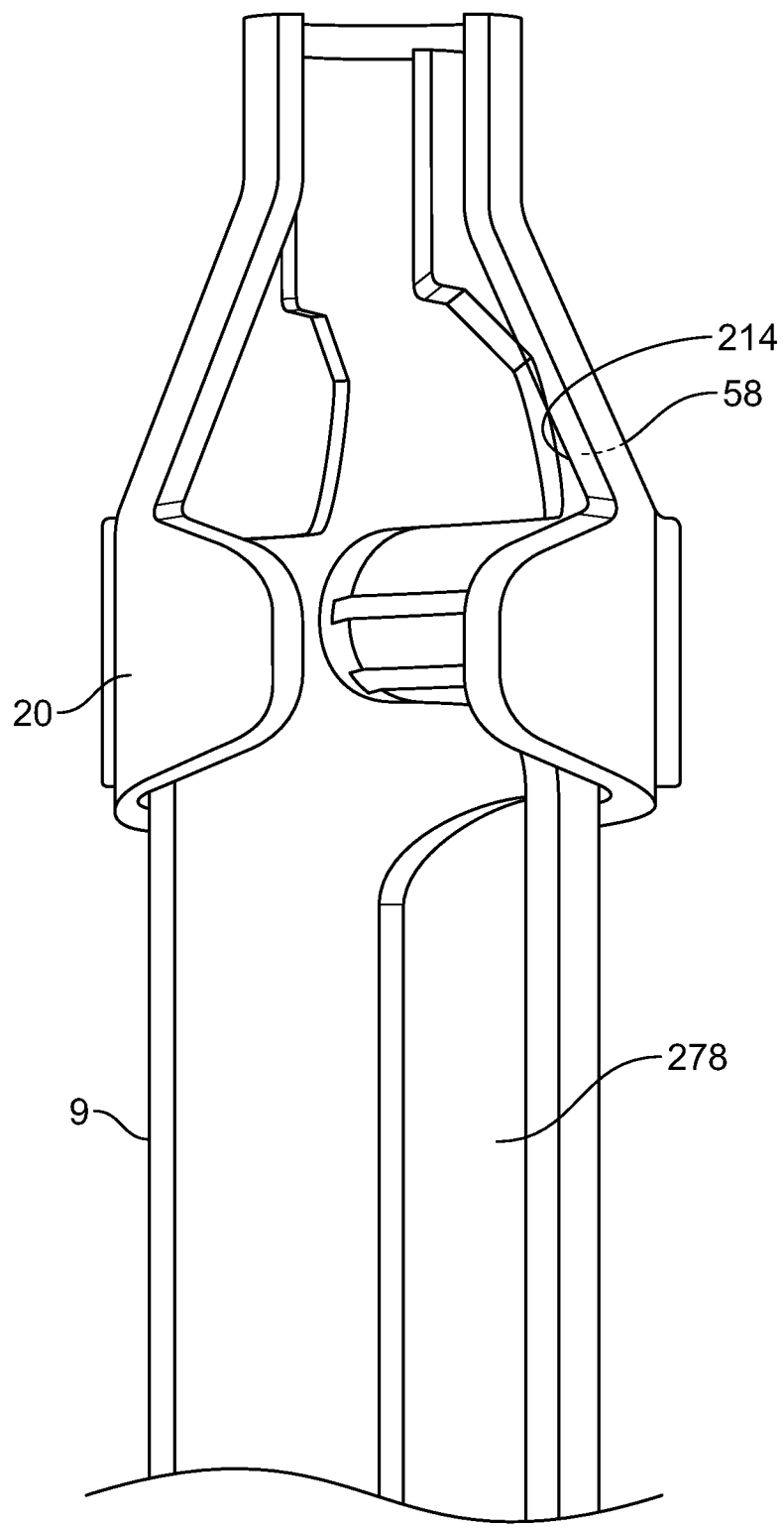
FIG. 13 is a front oblique side elevation of the sheath on the syringe.

At FIG. 13, topmost thread segment 58's leading point 214 (FIG. 13), is traveling along groove segment 95 (FIG. 12). But, leading point 214 encounters a constricted end 215 of groove 95, providing a low-resistance stop.

Increasing rotation force will force the sheath 20 to rotate again and accelerate briefly, as stop 152 (FIG. 8) drops into gap 200 (FIG. 12).

But, there is only about one millimeter of play before stop 151 stops hard against edge 160 (FIGS. 2 & 3). This centers sheath 20, so that sheath front wall gap 56 aligns with syringe front wall gap 64, (FIGS. 1 & 6) so that the needle assembly 14 can be inserted into the cone 16.

After insertion of the cone 15, this sheath 20 will be rotated 180 degrees so that the incline of thread 50 and grooves 39 push the needle assembly 14 needle-ward, to the position shown in FIG. 11, thereby seating a conical segment 15 of the needle assembly 14, against a cooperatively shaped conical part 140 of the interior of the syringe's cone 16.

Figure 22:
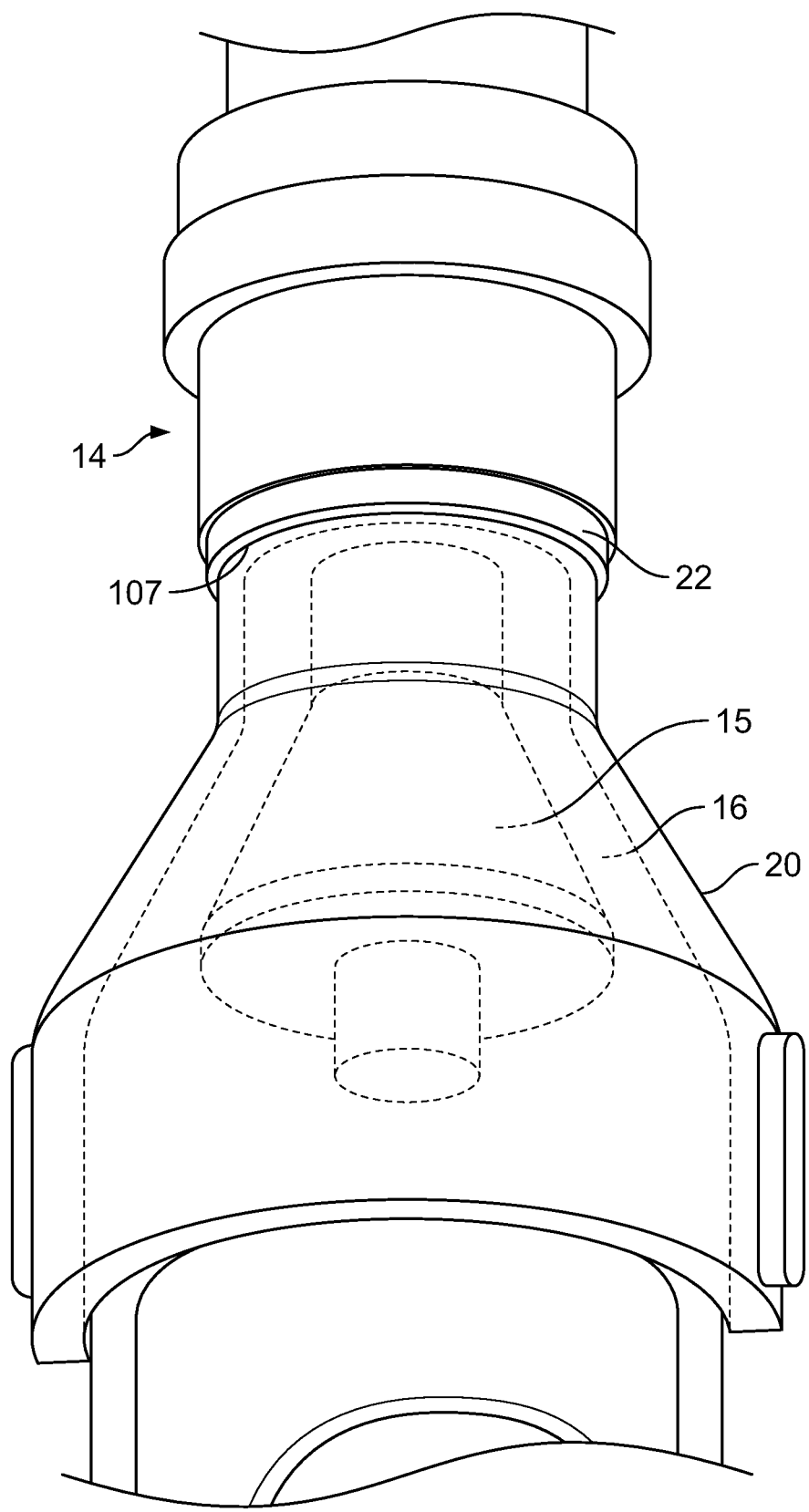
FIG. 22 is a perspective view of the syringe, with the sheath holding the needle assembly firmly in the syringe.

FIG. 22 shows how the top, or tip, or end 107 of sheath 20 abuts and pushes against flange 22 of needle assembly 14, thus seating needle's cone 15, firmly against the inside of syringe cone 16.

Sheath 20 will thus stabilize the needle assembly 14, and thereby facilitate installation of anesthetic medicine cartridges 12, and facilitate changing anesthetic medicine cartridges 12 during multiple injections.

Further tightening rotation of the sheath 20 will cause the flexible sheath's threads to jump the grooves on the syringe, allowing sheath 20 to move one groove ring-ward, and thereby relieve the seating pressure, and thereby allowing the needle assembly 14 to fall from the syringe 5 into a sharps container, not shown.

Alternatively, reversing rotation, to a loosening rotation of sheath 20, will relieve the seating pressure and allow the needle to fall from the syringe into a sharps container.

This sheath can be made out of stainless steel sheet to meet the above criteria. The stainless steel sheet can remove the chrome plating after multiple uses; therefore, there must be no sharp edges to remove chrome plating.

FIG. 13 shows multiple grooves to stabilize of the sheath on the syringes to allow forward rotation (the activated position) and backward (the resting position). I have tried the grooves in the cone section of the syringes; however, the grooves in the cone section do not add to the stability. These grooves should not hinder the placement (or removal) of cartridges; therefore, the grooves should not be placed below the ribbon part of the syringe.

Figure 14:
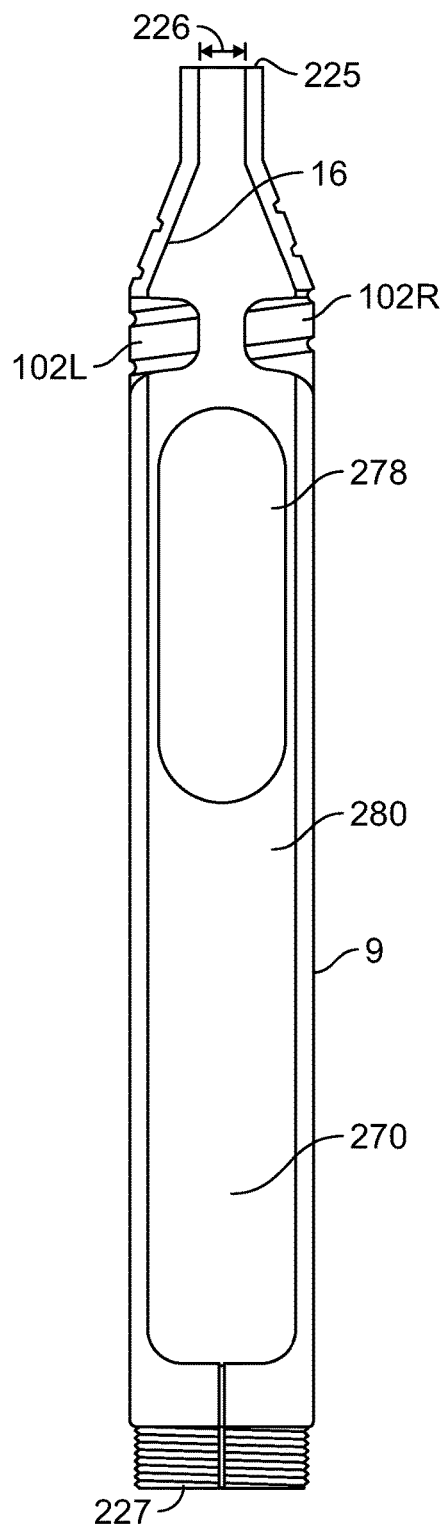
FIG. 14 is a front elevation of the syringe body.

FIG. 14 is a front elevation of an early embodiment of syringe body, generally designated 9, with threads running onto the cone.

Dimensions are provided in millimeters (mm). Body 9 has a tip-ward surface 225 measuring 5.2 mm across its outer diameter. Threads 227 at the bottom or ring-ward end of syringe body 9 can screw into finger grip 8 (FIG. 1), to assemble syringe body 9 to finger grip 8.

A 24.8 mm long slot 278 is provided, so that the user can change medicine cartridge 12 by:
 withdrawing the harpoon 11 FIG. 19, by pulling down (ring-ward) the shaft 10 13, pulled back by actuator ring 7 (FIG. 1);
 pushing a finger through ejection slot 278 from the back of syringe body 9 (FIGS. 14 & 19) against medicine cartridge 12 (FIG. 1);
 placing the thumb of the same hand as the finger against the front of medicine cartridge 12, to grasp medicine cartridge 12;
 sliding medicine cartridge 12 ringward or away from cartridge needle 231 and out front opening 280, to free medicine cartridge 12 from cartridge needle 231.

FIG. 14 is a front elevation of syringe 5 syringe body 9, showing slot 278, and dimensions in mm.

Figure 15:
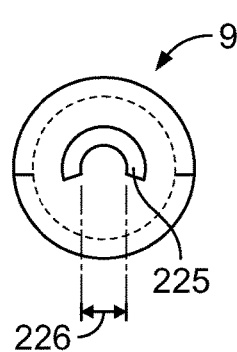
FIG. 15 is a top plan view thereof.

FIG. 15 is a top plan view of syringe body 9, showing top surface 225 of syringe body 9.

Figure 16:
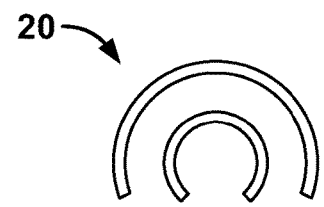
FIG. 16 is a top plan view of the sheath.

FIG. 16 is a top plan view of sheath 20.

Figure 17:
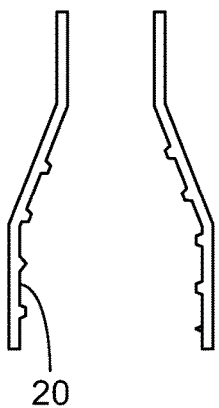
FIG. 17 is a front elevation thereof.

FIG. 17 is a front elevation of sheath 20.

Figure 18:
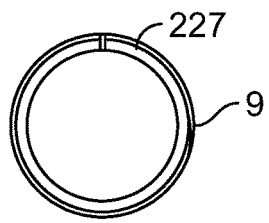
FIG. 18 is a plan view of the body.

FIG. 18 is a bottom plan view of syringe body 9, showing threads to mount the finger grip 8.

FIG. 19 is a front elevation of said syringe body 9 with plunger shaft 10 mounted on syringe body 9.

A collar 228 extends tip-ward from the syringe body 9. The collar 228 has a tip-ward edge 225.

A front collar opening 226 has a width 226A equal to the inner diameter of the collar 228. The front collar opening 226 extends the axial length 226B of the collar 228.

Figures 20, 20A:
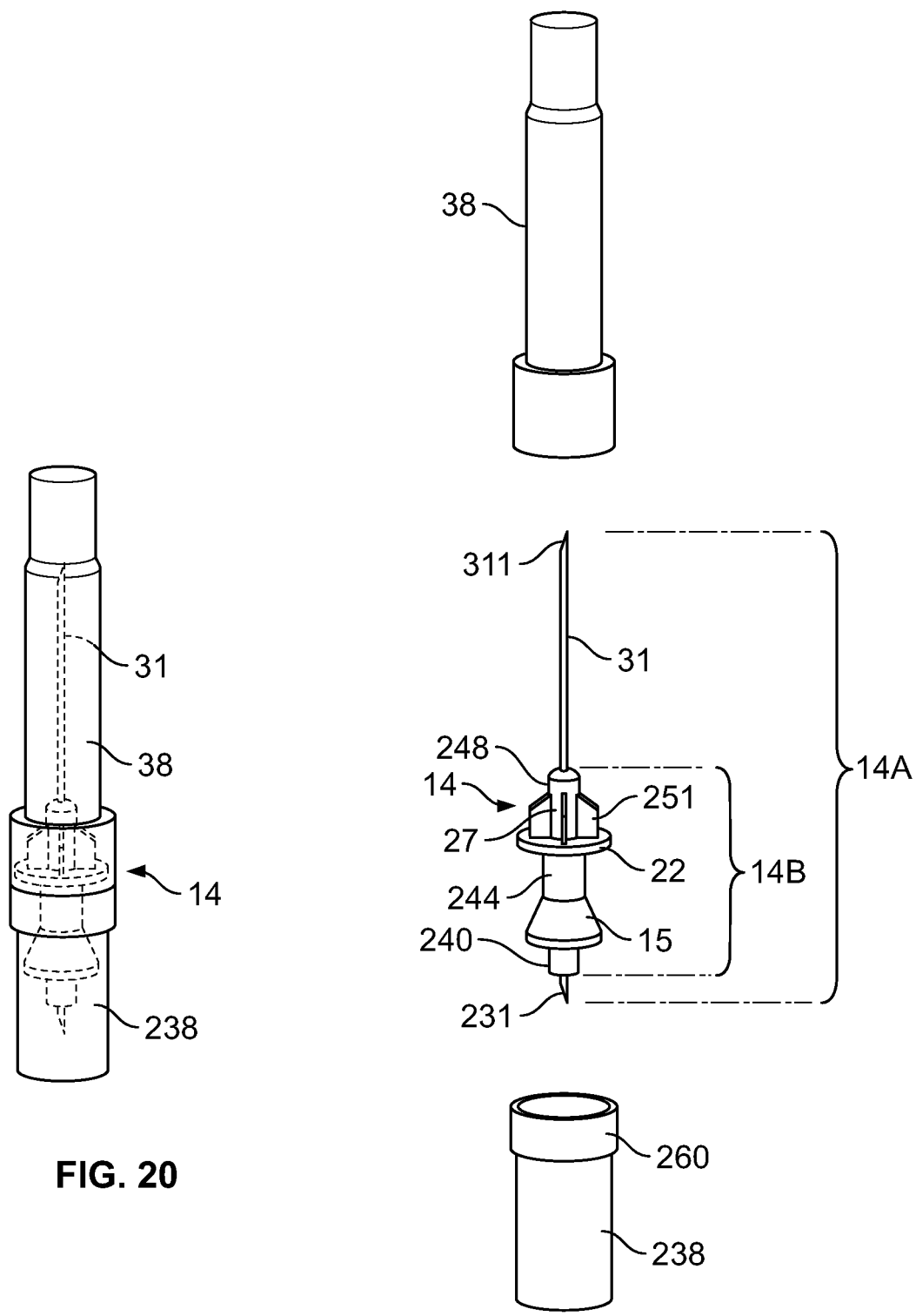
FIG. 20 is a perspective view of the needle assembly.
FIG. 20A an exploded view of the medicine cartridge.

FIG. 20 is a perspective view of a needle assembly 14. The needle assembly 14 is assembled. When the needle assembly 14 is assembled, protective cap 38 protects needle 31, to prevent needle 31 from stabbing a user accidentally.

Figure 21:
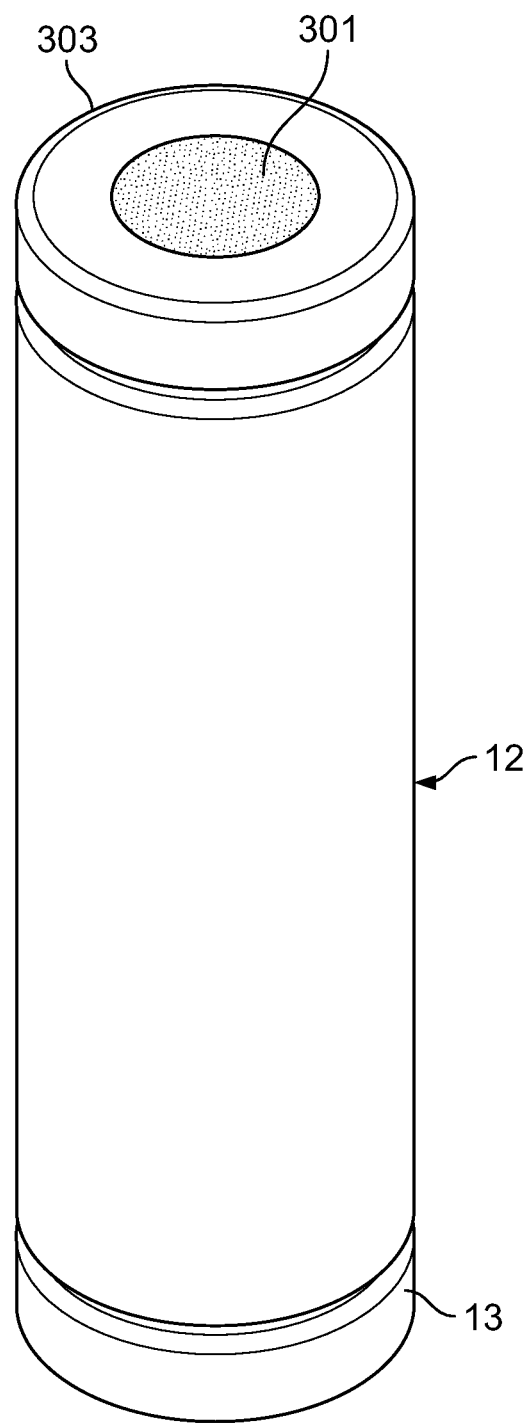
FIG. 21 is a perspective view of the medicine cartridge.

FIG. 21A shows needle assembly 14 is in three pieces on the right. Needle 31 is part of a needle tube 14A.

The opposite end of needle tube 14A is a second needle or cartridge needle 231 in fluid communication through needle tube 14A with needle 31, at the ring-ward end of needle assembly 14, under protective cap 238, when assembled.

Cartridge needle 231 is exposed, when uncapped, so that it may impale a diaphragm 301, atop cap 303 at a tip-ward end of medicine cartridge 12, establishing fluid communication from the medicine cartridge to the hollow needle tube 14A.

Needle tube reinforcement 14B reinforces needle tube 14A. Cylinder 240 reinforces the needle tube 14A at its cartridge-ward end. A second cylinder 244 is tip-ward of cone 15. This cylindrical form 244 carries up to its terminus at 248 where needle 31 is bare. A flange 22 is provided, for sheath 20's pushing against, as in FIG. 22. In FIG. 20, a plurality of six fins 251 reinforces structure 244 and flange 22. Fins 251 provide a snug fit to protective cap 38.

When cap 238 is in its protective position:
the widest part of cone 15 fits snugly against cap 238 in place; and
238's rim 260 abuts against a flange 22.

From needle-ward, in a plan view, the six fins 251 resemble an asterisk.

To install the needle assembly 14 onto the syringe, sheath 20 is snapped onto syringe body 9, as in FIG. 6, and syringe front walls 102L and 102R are aligned with sheath front walls 42L & 42R, to allow needle 231 of needle assembly 14 to pass through the gap formed between the left and right front walls of the sheath and the syringe.

Lower or ring-ward protective cap 238 is removed from lower or ring-ward needle 231 to expose ring-ward cartridge needle 231. The needle assembly 14 is placed with its cone 15 through the aligned front openings of syringe and sheath, with conical portion 15 of the needle assembly 14. Conical portion 15 is then seated inside the matching conical end 16 of syringe body 9, as in FIGS. 1 and 6.

Sheath 20 is then rotated in a clockwise direction, when viewed from the actuator ring 7, to be positioned as in FIG. 22, causing end 107 of sheath 20 screw to needle-ward, against flange 22, forcing the needle assembly 14, still-capped by needle-cap 38, needle-ward, so that cone 15 seats firmly against the inside of syringe cone 16, holding the needle assembly 14 firmly in place in the syringe body 9. The front gap of the sheath 20 is now aligned diametrically opposite to the front gap of syringe body 9, which closes the front opening 280. In the presently preferred embodiment, this is a 180 degree rotation from the open position.

Thumb ring 7 (FIG. 1) is then pulled down to clear the harpoon 11 (FIGS. 1 & 19), from the compartment 270 for the medicine cartridge 12, thus providing room for the medicine cartridge 12 to be inserted through opening 280 (FIG. 19).

Through the front opening 280 of compartment 270 (FIGS. 14 & 19), medicine cartridge 12 is then installed, and positioned as shown in FIG. 1.

Thumb ring 7 is then pressed by the user, down towards the needle;

driving shaft 10 and harpoon 11 into plunger 13 (FIG. 21) of medicine cartridge 12; driving the medicine cartridge 12 toward the needle assembly 14; and impaling the tip-ward diaphragm 301, located atop cap 330 of the medicine cartridge 12, by impaling the tip-ward diaphragm 301 on aft needle 231 of FIG. 20; and creating fluid communication between the medicine in medicine cartridge 12 and the hollow needle 31 and its hollow point 311 at tip 34.

Medicine cartridge 12 may thereafter be changed for this patient. Thumb ring 7 is withdrawn as far as possible which pulls harpoon 11 out of plunger 13 and provides clearance of the cartridge, probably disengaging the cartridge from aft needle 231. If the cartridge as not come loose of aft needle 231, the cartridge is grasped between a thumb (through opening 280) and forefinger (through opening 278), and pulled back from aft needle 231. Syringe 5 can then be turned front side down. Medicine cartridge 21 will then fall through opening 280 out of compartment 270.

A new medicine cartridge 12 may then be inserted as described above.

When the patient is done being anesthetized, the last cartridge can be removed, sheath 20 can be rotated in either direction, which will either:
twist sheath 20 away from flange 22 on needle assembly 14; or
allow with threads to jump next lower groove segment.

Either way, the pressure holding the flange 22 needle-ward, and holding cone 15 in its seat 16, is relieved. Then the syringe can be turned, front-down, allowing the needle assembly 14 to drop out of the syringe 5 into a sharps container.

The Slope of the Grooves.

The limitation of the activation position will be when the sheath 20 pushes the needle assembly 14 against the end of the syringe 5. But the slope of the grooves has to be such that, for a 120 degree rotation, the forward, or needle-ward, traveling length (from the resting to the activated position) is about 1.8-2.0 mm.

Sharps De-Tipping System

New matter in this United States Continuation-in part Application follows. The new matter comprises a system of removing the needle 31 from the syringe 3.

Figure 23:
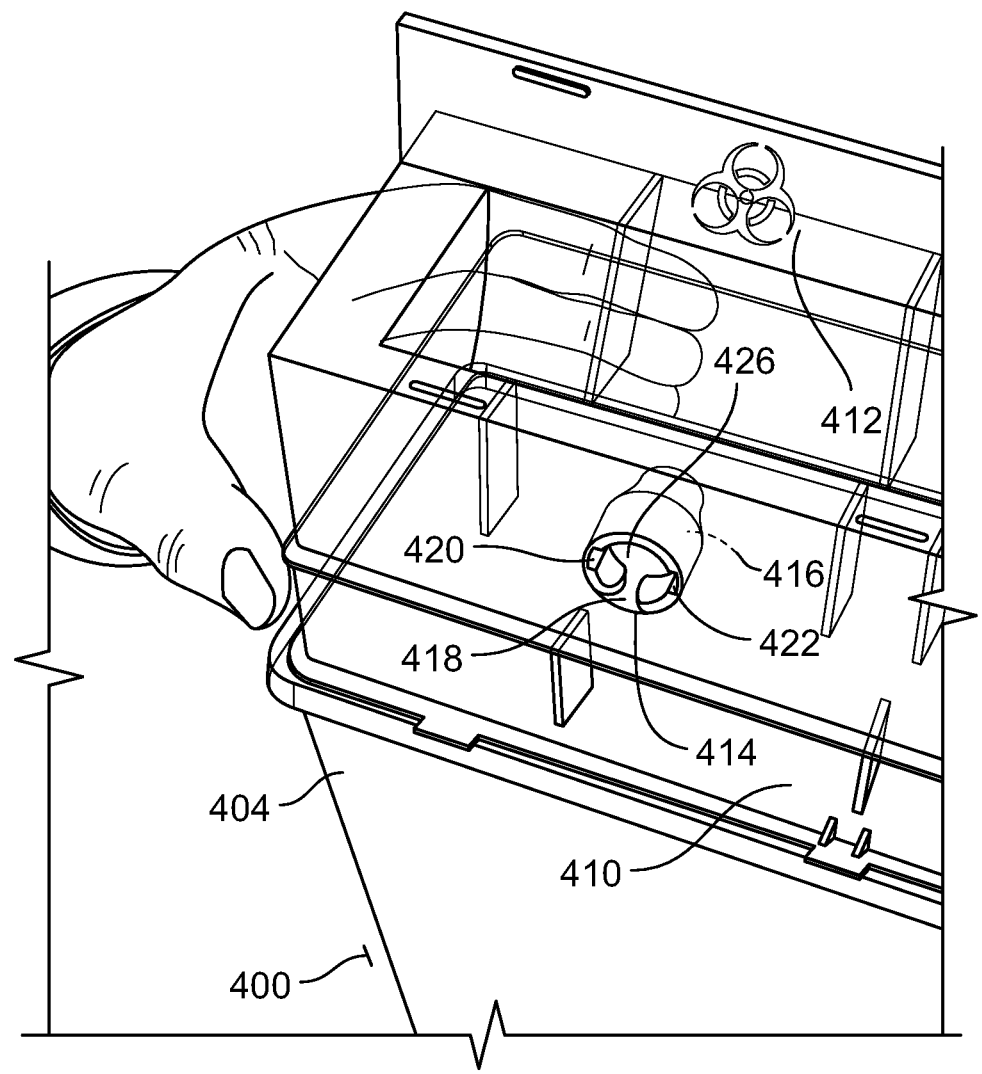
FIG. 23 is a perspective view of a sharps container.

FIG. 23 shows a sharps container generally designated 400. The sharps container comprises a sharps container bottom 404.

Atop to the sharps container bottom portion 404 is removably attached a sharps container in top 410. This conventionally includes a sharp container lid 412.

Sharps socket 414 is a novel part of this sharps container 400.

Sharps socket 414 has a front opening 418.

A left notch 420 and a right notch 422 in the opening 418 of socket 414 are configured to engage finger ribs 141 & 142, on the outside of sheath 20, shown in FIGS. 7 and 8.

As shown in FIG. 23, socket 414 has an interior surface 426 is configured to closely receive and frictionally engage an outer surface 428 (FIG. 24) of sheath 20.

Figure 24:
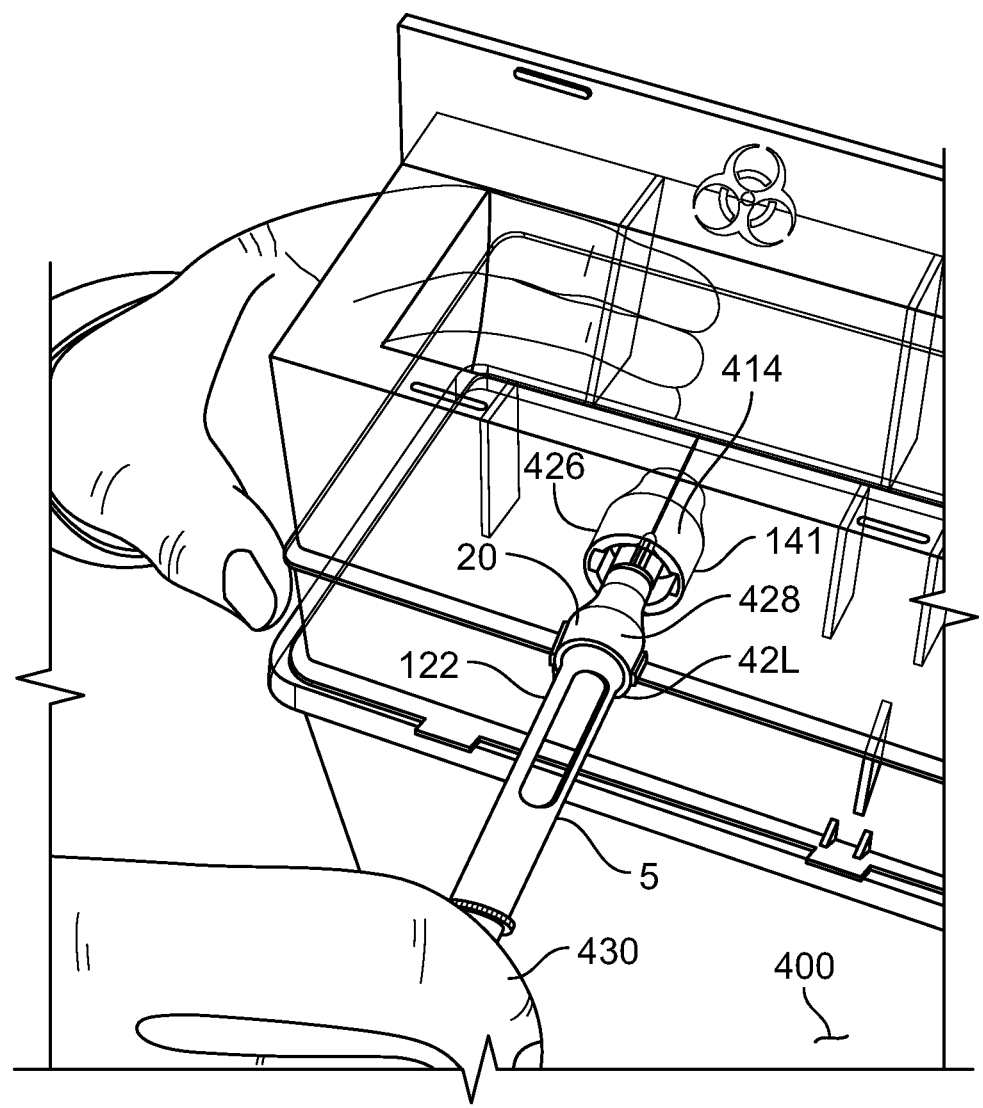
FIG. 24 is a perspective view of a sharps container and syringe while de-tipping.

FIG. 24 shows the syringe, generally designated 5, without its medicine cartridge, shown in FIG. 1 as medicine cartridge 12.

FIG. 24 shows the needle assembly 14A held in place by sheath 20. Screw threads that have been detailed in FIGS. 2 through 5, are holding the flange 22 by sheath 20's pushing against the flange 22, as in FIG. 22.

In FIG. 24, a user directs tip 34 of the needle 31 towards opening 418. Once the tip 34 is inside the opening 418, then needle, 31 needle assembly 14, and sheath 20 help guide sheath 20 into the socket 414.

The front 42 of sheath 20 is closed at gaps at 43, 44 (FIG. 10), and 45 to 46 (FIG. 9), to prevent needle assembly 14 from escaping the front body opening 122 in the syringe body 9.

FIG. 24 shows user 430 inserting sheath 20 into socket 414.

Rib 42L will enter notch 141 in sharps socket 414, pushed by user 430. Socket 20, is at an angle such that edge 42L of its sidewall defines a gap which does not align with front body opening 122. The rib 141 will be fully inserted into notch 422, which will prevent the sheath 20 from rotating with syringe 5.

User 430 will begin rotating syringe 5 in a clockwise direction 432. This rotation eventually causes the internal threads 52-58 of the sheath 20 to jump the grooves 91-95 of the syringe body 9 (see FIG. 5) and to relieve pressure on flange 22 of the needle assembly 14 shown in FIG. 20A.

Had syringe body 5 been rotated counterclockwise, the counterclockwise rotation would unscrew the internal threads 52-58 of the sheath 20 from the grooves 91-95 of the syringe body 9 (see FIG. 5) and, in that way, to also relieve pressure on flange 22 of the needle assembly 14 shown in FIG. 20A.

The syringe 5 has thus been rotated 180° from its original position. Opening 122 is now beneath the syringe 5 and is aligned with the opening in sheath 20. Pressure has been relieved from the flange 22; and a lack of tension against seat 15 allowed needle assembly 14A to fall through the gaps of syringe 5, and through sheath 20, through socket 414, into the bottom 404 of the sharps container shown in FIG. 23.

Next, syringe 5 is withdrawn from the sharps socket 414.

Figure 25:
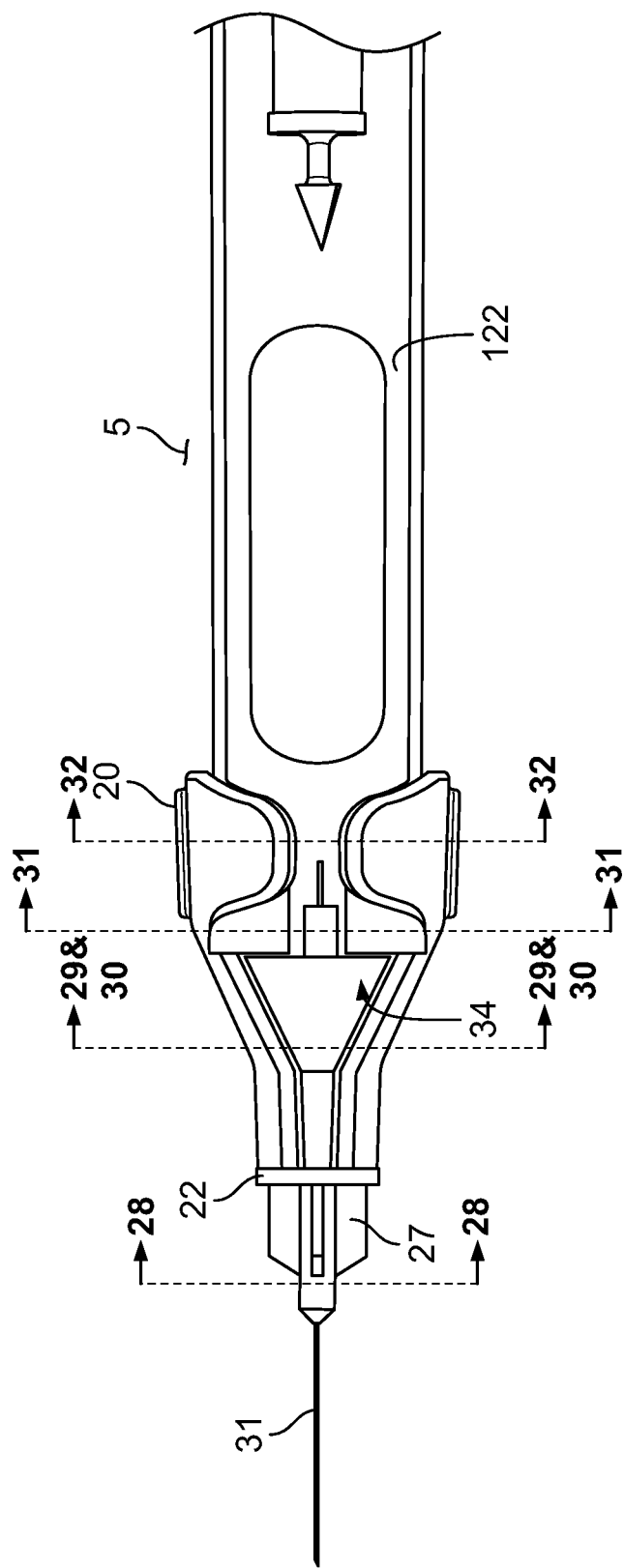
FIG. 25 is a front elevation of part of the dental syringe, without the cartridge, showing cross-sectional planes of FIGS. 28-32.
Figure 27:
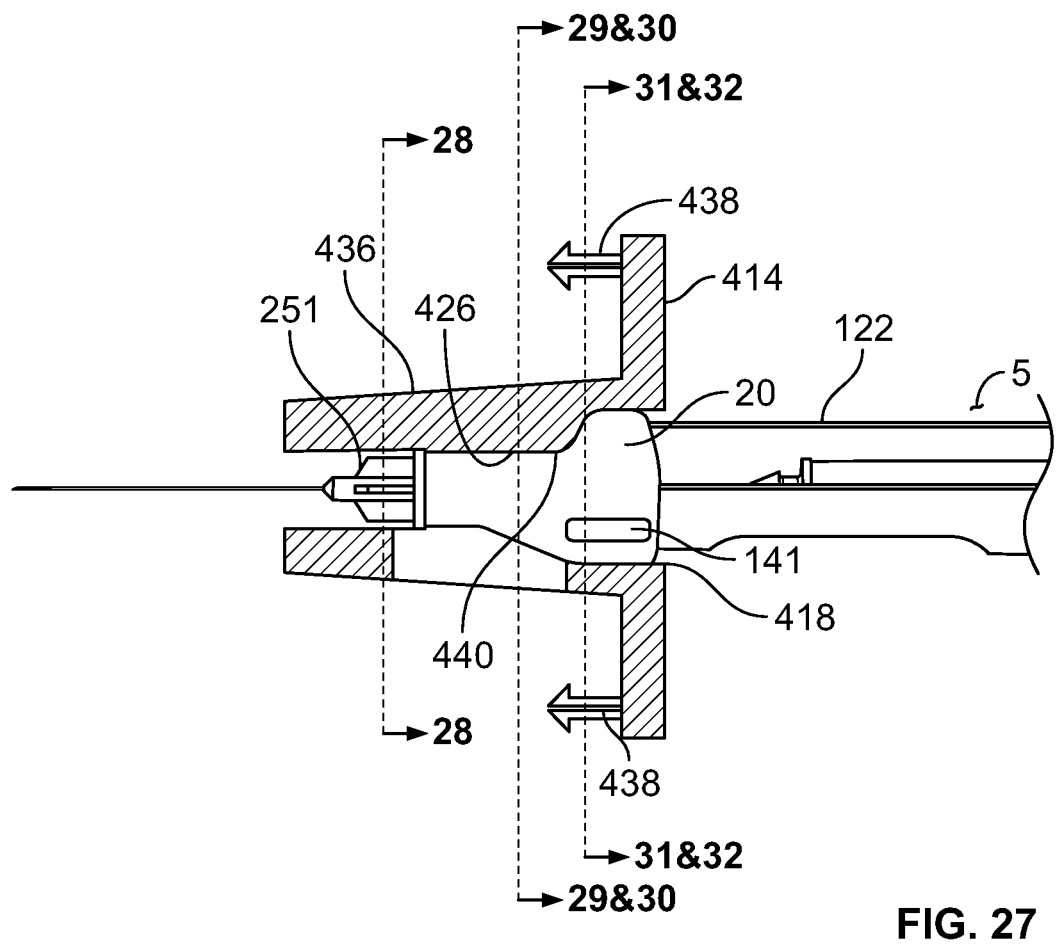
FIG. 27 is a side elevation of the syringe and a side elevation in section of the socket, showing cross-sectional planes taken through FIGS. 28-32.

FIG. 25 is added to show, from a front view of syringe 5, where the cross-sectional planes of FIG. 27 are in original FIG. 1 and in original FIG. 27.

In FIGS. 25 & 27 four planes are shown in cross section in FIGS. 26 through 34.

Figure 28:
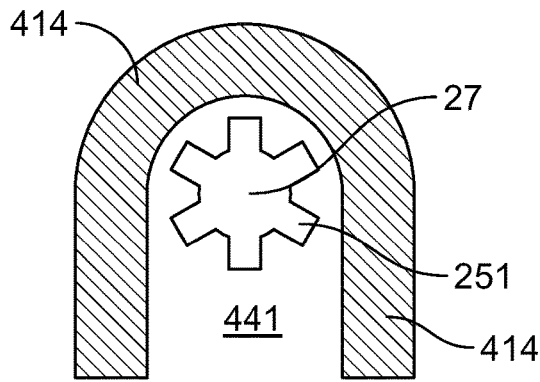
FIGS. 28-34 are cross sections taken through planes 28-34 defined in FIGS. 25 & 27.

Plane 28 shown in FIG. 28.
Plane 29 & 30 shown in FIGS. 29 & 30.
Plane 31 & 32 shown in FIGS. 31 & 32.
Plane 33 & 34 shown in FIGS. 33 & 34.

FIG. 25 is a side elevation of needle assembly with sheath 20 showing rib 141 and body front opening 122. The syringe 5 should be inserted in the sharps container 400 body with its body front opening 122 up. If the sheath 20's opening 43 is down, securing the needle assembly 14A to the syringe 5, then the sheath opening will be facing down, towards the sharps container bottom 404.

Figure 26:
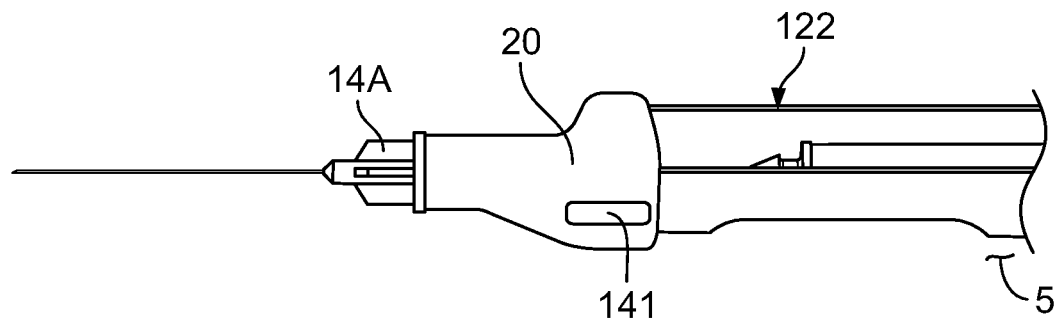
FIG. 26 is a side elevation of the syringe.

FIG. 26 is a cross-section of socket 414, but a side elevation of the outside surface 440 of sheath 20, fitted within socket 414. The close cooperative relation and snug fit, between:

sheath 440's inner surface 426, and
the sheath 20's external surface 440,
is clearly seen in FIG. 26.

Figure 29:
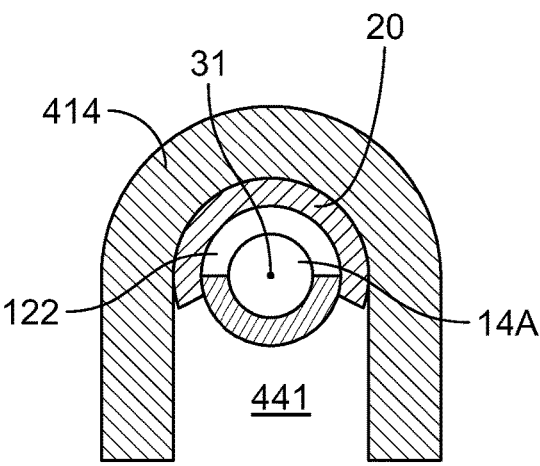
Figure 30:
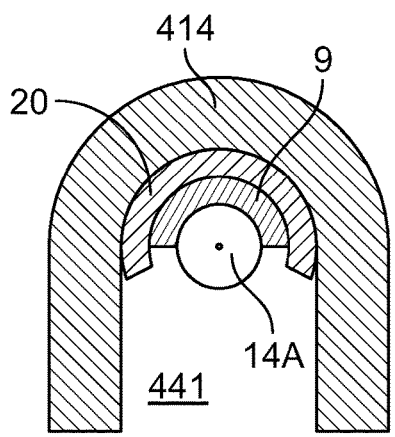
Figure 31:
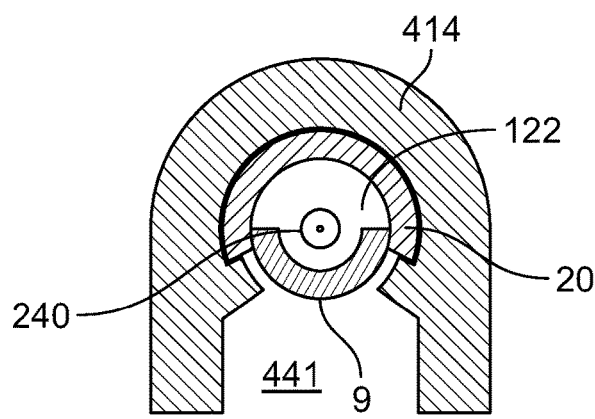
Figure 32:
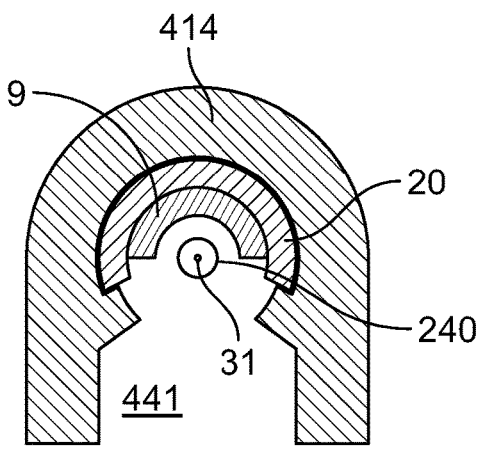
Figure 33:
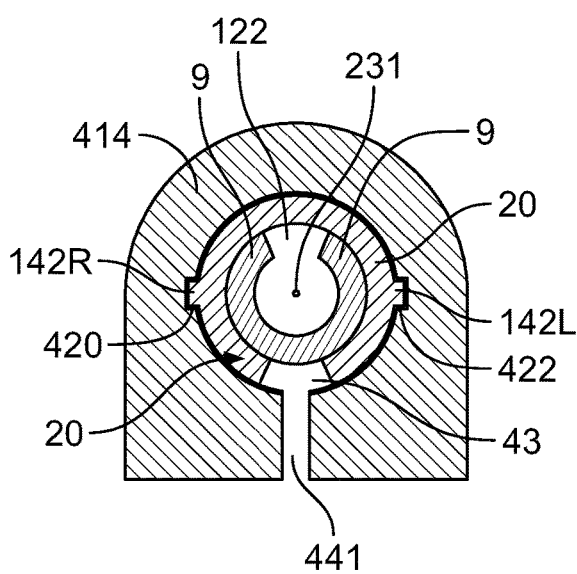
Figure 34:
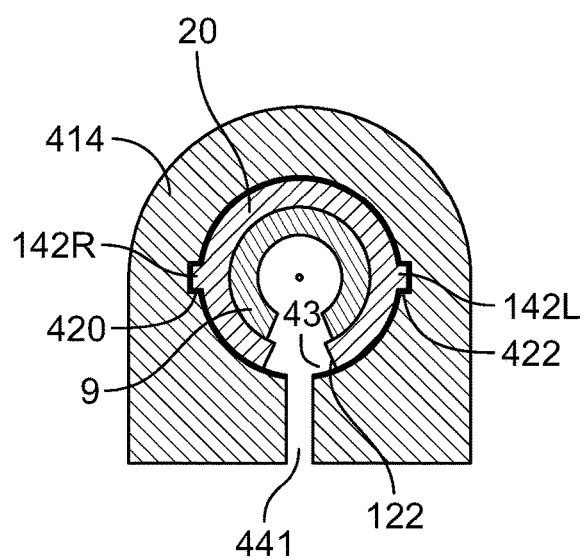

FIG. 27 again defines cross sectional planes, this time with the sheath 20 inserted into socket 414:

plane 28 of FIG. 28,
plane 29 & 30 of FIGS. 29 and 30,
plane 31 & 32 of FIGS. 31 and 32, and
plane 33 & 34 of FIGS. 33 and 34.

Socket 414 is preferably made of polypropylene, as is the sharps container. Snap-in fasteners 438 may protrude from the container-side of the socket 414. The snap-in fasteners 438 will snap into cooperatively sized fastener holes 439 in the sharps container top 410.

Socket 414 comprises an opening 441 in its bottom, for the sharps, also called the needle assembly 14A, to fall through, towards the sharps container bottom.

FIG. 29 is a cross section through plane 29 & 30 of FIGS. 25 & 27. Reinforcing fins 251 are visible in this cross-section.

FIG. 30 is similar to FIG. 29. FIG. 30 shows the syringe 9, rotated 180° from FIG. 28, and thus oriented so that sheath 20's opening 43 coincides with the syringe 5's body front opening 122 of frame 9; and therefore needle assembly 14A is free to drop out of the socket 414 and into the bottom 404 of the sharps container 400.

FIG. 31 is a cross-section of socket 414 at plane 31 of FIG. 25, showing the needle 31 passing through the needle assembly 14A at conical section 15. The posterior bump 240 assists in self-aspiration of the needle. Self aspiration enables the needle to withdraw any blood which may be in a blood vessel, if needle tip 34 is in a blood vessel. Such withdrawn blood can be seen in the medicine cartridge, through the body front opening or the back window. If blood is visible in the medicine cartridge, then the needle 31 must be withdrawn from the injection site, and inserted in an area where the needle 31 cannot inject anesthetic into a blood vessel. Injection of anesthetic into a blood vessel can cause unconsciousness, systemic reaction, or death In FIG. 31 the front body opening 122 of metal frame 9 does not coincide with open gaps of sheath 20, so that the needle assembly 14A cannot fall out.

FIG. 32 is similar to FIG. 31, a cross-section of socket 414 at plane 31 of FIGS. 25 & 27. FIG. 31 shows the syringe 9, rotated 180° from FIG. 30, and thus oriented so that sheath 20's opening 43 coincides with the syringe 5's body front opening 122 of frame 9; and thus needle assembly 14A is free to drop out of the socket 414 and into the bottom 414 of the sharps container 400.

FIG. 33 is a cross-section of socket 414 at plane 32 of FIGS. 25 & 27. In FIG. 33 the front body opening 122 of metal frame 9 does not coincide with open gaps of sheath 20, so that the needle assembly 14A cannot fall out. Sheath 20 comprises ribs 42R and 42L. At this plane 32, socket 414 comprises cooperating grooves 420 & 422, into which ribs 42R and 42L fit snugly, to prevent rotation of sheath 20, relative to socket 414. Thus, when syringe 5 and metal frame 9 are rotated 180°, as shown in FIG. 33, sheath 20 maintains its rotational position in the socket 414.

FIGS. 33 & 34 are cross-sections of socket 414 at plane 32 of FIGS. 25 & 27.

FIG. 34 is similar to FIG. 33. FIG. 34 shows the syringe 9, rotated 180° from FIG. 32, and thus oriented so that sheath 20's opening 43 coincides with the syringe 5's body front opening 122 of frame 9; and thus needle assembly 14A. is free to drop out of the socket 414 and into the bottom 404 of the sharps container 400.

The invention claimed is:

1. A cartridge syringe system comprising:
a syringe;
said syringe having a tip-ward direction and a ring-ward direction;
wherein said syringe comprises:
a syringe body;
an actuator ring;
a shaft slidably mounting said actuator ring to said syringe body;
a harpoon at a tip-ward end of said shaft; and
a sheath;
wherein said syringe body comprises a spiral body mount external to said syringe body configured to removably mount said sheath rotatably to the syringe body;
wherein said sheath has an internal spiral mount configured to removably mount said sheath rotatably to said spiral body mount external to said syringe body;
wherein
said sheath has a front sheath opening;
said syringe body has a body front;
said body front has a body front opening; and
said front sheath opening and said body front opening are configured of cooperatively similar size and shape so that said front sheath opening is rotatable to:
an open position, where said front sheath opening and said body front opening coincide, to permit installation of a needle assembly into said syringe body or removal of said needle assembly from said syringe body; or
a closed position, where said front sheath opening and said body front opening do not coincide, and thereby retain said needle assembly in said syringe body;
wherein
said internal spiral mount is an internal thread;
said spiral body mount is an external groove;
said internal thread is configured to rotatably mate with said external groove thereby rotatably mounting said sheath to said syringe body, mounting to said external groove on an outside of said syringe body;
wherein said sheath comprises:
a left sheath tab and a right sheath tab extending into said front sheath opening;
a pair of front wall tabs, comprising a left front wall tab and a right front wall tab extending from said syringe body into said body front opening;
wherein said left front wall tab is spaced from said right front wall tab by a gap and
in said closed position, one of said sheath tabs closes said gap;
wherein the cartridge syringe system further comprises:
a needle assembly;
said needle assembly comprising a needle tube having a needle tip, a cartridge needle and a tube reinforcement;
wherein
said body front opening has a plurality of varying body front opening widths;
said sheath opening has a plurality of varying sheath opening widths;
said varying sheath opening widths are configured to be rotatable, to coincide with said varying body front opening widths, to thereby open said body front opening;
and
said varying sheath opening widths are configured to be rotatable, to not coincide with said varying body front opening widths, and thereby to close said body front opening;
wherein said syringe body has an inside of a syringe cone having a tip-ward body opening width of said varying body front opening widths;
wherein said tip-ward body opening width is configured:
to allow said tube reinforcement to pass through said tip-ward body opening width and said tip-ward sheath opening width when said tip-ward body opening width and said tip-ward sheath opening width coincide; and
to retain said tube reinforcement when said tip-ward body opening width and said tip-ward sheath opening width do not coincide.

2. A cartridge syringe system according to claim 1, in which the tube reinforcement, has:
a cylindrical portion
a flange; and
a conical portion.

3. A cartridge syringe system according to claim 2, in which the cylindrical portion is braced to the flange by a plurality of radial fins.

4. A cartridge syringe system according to claim 3, in which the radial fins are configured to removably friction mount a safety cap to the needle assembly.

5. A cartridge syringe system according to claim 4, in which the safety cap is configured to removably friction mount a rim of a cartridge-ward safety cap to the needle assembly.

6. A cartridge syringe system according to claim 5, in which:
the needle assembly further comprises an assembly conical portion of the needle assembly;
the syringe body further comprises a body conical end; and
the assembly conical portion seats against the body conical end.

7. A cartridge syringe system according to claim 6, in which, rotating the sheath from the seated position:
I. unseats the needle assembly from the syringe body;
II. coincides the sheath opening widths with the varying body front opening widths and thereby opens the body front opening; and
III. allows the tube reinforcement to pass through a tip-ward body opening width and the tip-ward sheath opening width when coincided;
for disposal of the needle assembly from the body.

8. A cartridge syringe system according to claim 7, in which the sheath has:
an outer circumference; and
a grip rib on said outer circumference.

9. A cartridge syringe system according to claim 8, in which the sheath has an opposite grip rib on an opposite side of said outer circumference.

10. A method of using a cartridge syringe system, said cartridge syringe system including:
a sheath;
said sheath having an internal sheath thread, spiraling inside the sheath;
a syringe body having an external body thread configured to screw to the internal sheath thread;
a needle assembly;
said needle assembly comprising a molded reinforcement;
said method comprising the steps of:
placing the sheath coaxially tip-ward of the syringe body;
pushing the sheath ring-ward onto the syringe body;
thereby:
deforming the sheath open, to engage the internal sheath thread to the external body thread; and to thereby secure the sheath to the syringe body;

aligning an opening in the sheath to a similarly configured opening in the syringe body;
inserting the molded reinforcement of the needle assembly through:
said aligned opening in the sheath, and
the opening in the syringe body;
rotating said aligned opening in the sheath out of alignment to the opening in the syringe body, to:
thereby retain the needle assembly to the syringe body; and
drive a flange of the needle assembly needle-ward; and
thereby seat a conical part of the needle assembly against a conical part of the syringe body;
inserting a diaphragm of a medicine cartridge through a cartridge opening into a compartment in the syringe body;
impaling a diaphragm of the medicine cartridge onto a ring-ward point of the needle;
seating a remainder of the medicine cartridge in the syringe body;
moving an actuator ring needle-ward;
thereby moving a shaft with a harpoon on an end of the shaft tip-ward towards the medicine cartridge;
thereby impaling a sliding seal in the medicine cartridge with the harpoon on the shaft, to form a plunger;
driving the plunger tip-ward to fill the needle with a medicine;
penetrating a target with the needle;
withdrawing the plunger, to test whether a tip of the needle is in a blood vessel; and
then injecting the medicine from the medicine cartridge into the target.

11. A method of using a cartridge syringe system, according to claim 10, said method including the further steps of:
withdrawing the harpoon from the medicine cartridge;
aligning the opening in the sheath to the similarly configured opening in the syringe body; and
pushing the medicine cartridge from a back hole in the syringe body to eject the medicine cartridge through a front opening (280) in the syringe body.

12. A method of using a cartridge syringe system, according to claim 11, said method including the further steps of:
inserting a diaphragm of a new medicine cartridge which new medicine cartridge is full, through a cartridge opening into a compartment in the syringe body;
impaling a diaphragm of the new medicine cartridge onto a ring-ward point of the needle;
seating a remainder of the new medicine cartridge in the body;
moving the actuator ring needle-ward;
thereby moving a shaft, with a harpoon on an end of the shaft towards the medicine cartridge;
thereby impaling the sliding seal in the medicine cartridge with the harpoon on the shaft, to again form the plunger;
driving the plunger tip-ward to fill the needle with a medicine;
penetrating a target with the needle; and
then injecting the medicine from the medicine cartridge into the target;
repeating the steps of claim 11 and of this present claim until a procedure is done, and there is no further need to administer more medication;
aligning the opening in the sheath to the similarly configured opening in the syringe body;
ejecting the molded reinforcement of the needle assembly through:
said aligned opening in the sheath, and
the opening in the syringe body; and
into a sharps container.

\* \* \* \* \*